(12) United States Patent
Nelson et al.

(10) Patent No.: US 8,202,972 B2
(45) Date of Patent: Jun. 19, 2012

(54) ISOTHERMAL DNA AMPLIFICATION

(75) Inventors: John Richard Nelson, Clifton Park, NY (US); Robert Scott Duthie, Schenectady, NY (US); Carl Williams Fuller, Berkeley, NJ (US); Gregory Andrew Grossmann, Halfmoon, NY (US); Anuradha Sekher, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1009 days.

(21) Appl. No.: 11/621,703

(22) Filed: Jan. 10, 2007

(65) Prior Publication Data

US 2009/0011472 A1    Jan. 8, 2009

(51) Int. Cl.
    *C07H 19/00*    (2006.01)
    *C12Q 1/68*     (2006.01)
    *C07H 21/04*    (2006.01)

(52) U.S. Cl. .................. 536/22.1; 435/6; 536/24.33

(58) Field of Classification Search ................ 536/22.1; 435/6, 91.2
    See application file for complete search history.

(56) References Cited

U.S. PATENT DOCUMENTS

| | | | |
|---|---|---|---|
| 5,866,336 A | 2/1999 | Nazarenko et al. | |
| 6,951,722 B2 * | 10/2005 | Mukai et al. | 435/6 |
| 7,198,894 B2 * | 4/2007 | Barany et al. | 435/6 |
| 2001/0041334 A1 * | 11/2001 | Rashtchian et al. | 435/6 |
| 2003/0104431 A1 | 6/2003 | Van Ness | |
| 2003/0228620 A1 * | 12/2003 | Du Breuil Lastrucci | 435/6 |
| 2004/0067559 A1 | 4/2004 | McCarthy et al. | |
| 2007/0020639 A1 * | 1/2007 | Shapero | 435/6 |
| 2007/0148636 A1 * | 6/2007 | Song et al. | 435/5 |

FOREIGN PATENT DOCUMENTS

| | | |
|---|---|---|
| EP | 1167524 A1 | 1/2002 |
| EP | 2050819 A1 | 4/2009 |
| WO | 0236821 A2 | 5/2002 |
| WO | 2004003232 A1 | 1/2004 |
| WO | WO 2006/125267 | * 11/2006 |
| WO | 2008013010 A1 | 1/2008 |

OTHER PUBLICATIONS

Hong Feng, et al., "Catalytic Mechanism of Endonuclease V: A Catalytic and Regulatory Two-Metal Model", Biochemistry, 2006, pp. 10251-10259, vol. 45.

Min Yao, et al., "Further Characterization of *Escherichia coli* Endonuclease V", Journal of Biological Chemistry, Dec. 5, 1997, pp. 30774-30779, vol. 272, No. 49.

Jiang Liu, et al., "A Deoxyinosine specific endonuclease from hyperthemophile, *Archaeoglobus fulgidus*: a homolog of *Escherichia coli* endonuclease V", Mutat. Res., Nov. 9, 2000, pp. 169-177, vol. 461.

Thomas M. Hitchcock, et al., "Cleavage of deoxyoxanosine-containing oligodeoxyribonucleotides by bacterial endonuclease V", Nucleic Acids Research, 2004, pp. 4071-4080, vol. 32, No. 13.

G. Terrance Walker et al., Isothermal in vitro amplification of DNA by a restriction enzyme/DNA polymerase system, Proc. Nati. Acad. Sci. USA vol. 89, pp. 392-396 (Jan. 1992).

Search Report of Jul. 22, 2008 PCT/US2008/050555.

* cited by examiner

*Primary Examiner* — Prabha Chunduru
(74) *Attorney, Agent, or Firm* — Jenifer E. Haeckl

(57) ABSTRACT

Provided herein are nucleic acid synthesis methods and agents that employ an endonuclease for example, endonuclease V, to introduce a nick into a target DNA including one or more inosine, and uses a DNA polymerase to generate amplicons of the target DNA.

22 Claims, 16 Drawing Sheets

SEQUENCE LISTING

<160> NUMBER OF SEQ ID NOS: 55

<210> SEQ ID NO 1
<211> LENGTH: 223
<212> TYPE: PRT
<213> ORGANISM: Escherichia coli

<400> SEQUENCE: 1

Met Asp Leu Ala Ser Leu Arg Ala Gln Gln Asn Glu Leu Ala Ser Ser
1               5                   10                  15

Val Asn Arg Glu Asp Arg Leu Asp Lys Asp Pro Pro Asp Leu Asn Ala
            20                  25                  30

Gly Ala Asp Val Gly Phe Glu Gln Gly Gly Glu Val Thr Arg Ala Ala
        35                  40                  45

Met Val Leu Leu Lys Tyr Pro Ser Leu Glu Leu Val Glu Tyr Lys Val
    50                  55                  60

Ala Arg Asn Ala Thr Thr Met Pro Tyr Asn Pro Gly Phe Leu Ser Phe
65                  70                  75                  80

Arg Glu Tyr Pro Ala Leu Leu Ala Ala Trp Glu Met Leu Ser Gln Lys
                85                  90                  95

Pro Asp Leu Val Phe Val Asp Gly His Gly Asn Ser His Pro Arg Arg
            100                 105                 110

Leu Gly Val Ala Ser His Phe Gly Leu Leu Val Asp Val Pro Thr Asn
            115                 120                 125

Gly Val Ala Lys Lys Arg Leu Cys Gly Lys Phe Glu Pro Leu Ser Ser
130                 135                 140

Glu Pro Gly Ala Leu Ala Pro Leu Met Asp Lys Gly Glu Gln Leu Ala
145                 150                 155                 160

Trp Val Trp Arg Ser Lys Ala Arg Cys Asn Pro Leu Phe Asn Ala Thr
            165                 170                 175

Gly His Arg Val Ser Val Asp Ser Ala Leu Ala Trp Val Gln Arg Cys
            180                 185                 190

Met Lys Gly Tyr Arg Leu Pro Glu Pro Thr Arg Trp Ala Asp Ala Val
            195                 200                 205

Ala Ser Glu Arg Pro Ala Phe Val Arg Tyr Thr Ala Asn Gln Pro
            210                 215                 220

<210> SEQ ID NO 2
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Leu Ala Ser Leu Arg Ala Gln Gln Asn Glu Leu Ala Ser Ser
1               5                   10                  15

Val Asn Arg Glu Asp Arg Leu Asp Lys Asp Pro Pro Asp Leu Asn Ala
            20                  25                  30

Gly Ala Asp Val Gly Phe Glu Gln Gly Gly Glu Val Thr Arg Ala Ala
            35                  40                  45

Met Val Leu Leu Lys Tyr Pro Ser Leu Glu Leu Val Glu Tyr Lys Val
50                  55                  60

Ala Arg Asn Ala Thr Thr Met Pro Ala Asn Pro Gly Phe Leu Ser Phe
65                  70                  75                  80

Arg Glu Tyr Pro Ala Leu Leu Ala Ala Trp Glu Met Leu Ser Gln Lys
            85                  90                  95

Pro Asp Leu Val Phe Val Asp Gly His Gly Asn Ser His Pro Arg Arg
            100                 105                 110

Leu Gly Val Ala Ser His Phe Gly Leu Leu Val Asp Val Pro Thr Asn
            115                 120                 125

Gly Val Ala Lys Lys Arg Leu Cys Gly Lys Phe Glu Pro Leu Ser Ser
130                 135                 140

Glu Pro Gly Ala Leu Ala Pro Leu Met Asp Lys Gly Glu Gln Leu Ala
145                 150                 155                 160

Trp Val Trp Arg Ser Lys Ala Arg Cys Asn Pro Leu Phe Asn Ala Thr
            165                 170                 175

Gly His Arg Val Ser Val Asp Ser Ala Leu Ala Trp Val Gln Arg Cys
            180                 185                 190

Met Lys Gly Tyr Arg Leu Pro Glu Pro Thr Arg Trp Ala Asp Ala Val
            195                 200                 205

Ala Ser Glu Arg Pro Ala Phe Val Arg Tyr Thr Ala Asn Gln Pro Leu
            210                 215                 220

Glu
225

<210> SEQ ID NO 3
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Leu Gln Met Asn Leu Glu Glu Leu Arg Arg Asn Gln Glu Glu Met
1               5                   10                  15

Ser Arg Ser Val Val Leu Glu Asp Leu Asn Pro Leu Glu Glu Leu Glu
            20                  25                  30

Tyr Val Val Gly Val Asp Gln Ala Phe Asn Ser Asp Glu Val Val Ser
        35                  40                  45

Cys Ala Val Lys Leu Thr Phe Pro Glu Leu Glu Val Val Asp Lys Ala
    50                  55                  60

Val Arg Val Glu Lys Val Thr Phe Pro Ala Asn Pro Thr Phe Leu Met
65                  70                  75                  80

Phe Arg Glu Gly Glu Pro Ala Val Asn Ala Val Lys Gly Leu Val Asp
                85                  90                  95

Asp Arg Ala Ala Asn Met Val Asp Gly Ser Gly Asn Ala His Pro Arg
            100                 105                 110

Arg Cys Gly Leu Ala Thr Tyr Asn Ala Leu Lys Leu Arg Lys Pro Thr
        115                 120                 125

Val Gly Asn Thr Lys Lys Arg Leu Phe Gly Glu Met Val Glu Val Glu
    130                 135                 140

Asp Gly Leu Trp Arg Leu Leu Asp Gly Ser Glu Thr Asn Gly Tyr Ala
145                 150                 155                 160

Leu Lys Ser Cys Arg Arg Cys Lys Pro Asn Phe Asn Ser Pro Gly Ser
                165                 170                 175

Tyr Asn Ser Pro Asp Ser Ala Leu Glu Leu Thr Arg Lys Cys Leu Lys
            180                 185                 190

Gly Tyr Lys Leu Pro Glu Pro Asn Arg Asn Ala Asp Lys Leu Thr Lys
        195                 200                 205

Glu Val Lys Arg Glu Leu Thr Pro Thr Ser Lys Leu Lys
    210                 215                 220

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caattgtaat ttctgtacgt ctcttatcat tgaagcgctc ttttacttct gttaattctt    60
cacgaataat ctcaaga                                                   77

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)

<223> OTHER INFORMATION: Inosine

<400> SEQUENCE: 5
tcttgagatt attcnt                                                        16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 6
caattgtaat ttctnt                                                        16

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (51)..(51)
<223> OTHER INFORMATION: Dideoxycytosine

<400> SEQUENCE: 7
aaattaatac gactcactat agggtgaaga attaacagaa gtaaaagagc c                 51

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaattaatac gactcactat agggttgaag aattaacaga agtaaaagag a                 51

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaattaatac gactcactat agggtgaaga attaacagaa g                            41

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (51)..(51)
<223> OTHER INFORMATION: Dideoxycytosine

<400> SEQUENCE: 10

```
aaattaatac gactcactat agggttgaag aattaacaga agtaaaagag c         51
```

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 11

```
tcgctgaatt aaaanc                                                16
```

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 12

```
atcaagattt aatgaant                                              18
```

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 13

```
tgttctggaa tcaant                                                16
```

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 14

```
aacgtaatgg cgatnt                                                16
```

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<221> NAME/KEY: modified_base
<222> LOCATION: (15)..(15)
<223> OTHER INFORMATION: Inosine

<400> SEQUENCE: 15
ttagatatgc gtctnc                                                     16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 16
gcttaacagg attana                                                     16

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 17
cgaaaaaatt gaacaana                                                   18

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 18
cagatgaaga aaagnt                                                     16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 19
cttcatcttc aatana                                                     16

<210> SEQ ID NO 20
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 20
aatataacca ttatgant                                                 18

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

<400> SEQUENCE: 21
tacgtagaag ctgnc                                                    15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

<400> SEQUENCE: 22
accacggttc tgtnt                                                    15

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccctatagtg agtcgtatta attt                                          24

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine

<400> SEQUENCE: 24
ggtcgactna ggaggatccc cgggtac                                       27

<210> SEQ ID NO 25
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccggggatcc tcctcagtcg acctgca                                           27

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagatataca tatggatctc gcg                                               23

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaatcgccgg catggtggtg gcgatgcg                                          28

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
accatgccgg cgattccagg ttttctttcc ttc                                    33

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tggtgctcga ggggctgatt tgatg                                             25

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatattcatc aatcggagta cgttttc                                           27

<210> SEQ ID NO 31
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
acaatcaaca acaagcacga attcgag                                          27

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: Inosine

<400> SEQUENCE: 32
agttcttctt tcgtccccnt                                                  20

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: Inosine

<400> SEQUENCE: 33
caggctgaca tcacnnt                                                     17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: Inosine

<400> SEQUENCE: 34
tcagttgttc acccagcna                                                   19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: Inosine

<400> SEQUENCE: 35
gcggagacgg gcaatcant                                                   19

<210> SEQ ID NO 36
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: Inosine

<400> SEQUENCE: 36
tcatctttcg tcatnna                                                    17

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: Inosine

<400> SEQUENCE: 37
tccacagaga aacaatnnc                                                  19

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: Inosine

<400> SEQUENCE: 38
accaccggcg atccnnc                                                    17

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: Inosine

<400> SEQUENCE: 39
gcgtgagttc accatna                                                    17

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Inosine

<400> SEQUENCE: 40
ttcagtcagc accgctna                                                   18
```

```
<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Inosine

<400> SEQUENCE: 41
tgatgctgct ggctna                                                    16

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: Inosine

<400> SEQUENCE: 42
ccctgatgag ttcgtnt                                                   17

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

<400> SEQUENCE: 43
ccgtacaact ggcnt                                                     15

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atgactggtg gacagcaaat gggtaaatta atacgactca ctatagggtt               50

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccctatagtg agtcgtatta attt                                           24

<210> SEQ ID NO 46
```

<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
ttgctgtcca ccagttac                                                 18

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (32)..(32)
<223> OTHER INFORMATION: Inosine

<400> SEQUENCE: 47
gttttcccag tcacgacgtt gtaaaacgac gncc                               34

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tcaaagaagt attgctacaa cgg                                           23

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gttttcccag tcacgacgtt gtaaaacgac ggcc                               34

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tcaaagaagt attgctacaa cgg                                           23

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (32)..(32)
<223> OTHER INFORMATION: Inosine

<400> SEQUENCE: 51
gcagatgaag aaaaggttct tgagattatt cnt                            33

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (51)..(51)
<223> OTHER INFORMATION: Dideoxycytosine

<400> SEQUENCE: 52
aaattaatac gactcactat agggttgaag aattaacaga agtaaaagag c         51

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: Inosine

<400> SEQUENCE: 53
tgctgctggc tgaccctna                                            19

<210> SEQ ID NO 54
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caatagactc cataccacca attgtaattt ctgtacgtct cttatcattg aagcgctctt    60
ttacttctgt taattcttca cgaataatct caagaacctt ttcttcatct gc          112

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: Inosine

<400> SEQUENCE: 55
caatagactc cataccacca attgtaattt ctnt                            34

ISOTHERMAL DNA AMPLIFICATION

FIELD OF THE INVENTION

The present invention generally relates to nucleic acid synthesis methods and agents that employ an endonuclease, for example, endonuclease V, to introduce a nick into a target DNA including one or more 2' deoxyinosine nucleosides, and employs a DNA polymerase to amplify a specific sequence DNA target.

INCORPORATION BY REFERENCE

This application incorporates by reference the Sequence Listing contained on the two compact discs (Copy 1 and Copy 2) containing the following file:

File name: "204091-1.ST25.txt" created Apr. 2, 2007, which is 13.1 kb in size.

BACKGROUND

DNA replication is the process of copying single or double-stranded DNA. Because DNA strands are antiparallel and complementary, each strand may serve as a template for the reproduction of the opposite strand by a DNA polymerase. The template strand is preserved as a whole or as a truncated portion and the new strand is assembled from nucleoside triphosphates.

In polymerase chain reaction (PCR), the target DNA, a pair of primers, and a DNA polymerase are combined and subjected to repeated temperature changes that permit melting, annealing, and elongation steps. The melting or denaturation step typically occurs at a high temperature limiting the choice of polymerases to thermophilic polymerases.

Endonuclease V (also called endo V or inosine 3' endonuclease) is a DNA repair enzyme first described in E. coli that recognizes DNA containing nucleotides with deaminated or otherwise modified bases such as inosine. Endonuclease V cleaves the second or third phosphodiester bond 3' to the inosine in the same strand leaving a nick with 3'-hydroxyl and 5'-phosphate. DNA polymerases add nucleotides to the 3' end of a pre-existing DNA strand resulting in 5'→3' elongation in a template-directed fashion to create a complementary strand.

BRIEF DESCRIPTION

Provided herein are methods, agents, and kits for producing an amplification product using a target DNA. In some embodiments, the methods comprise the steps of (a) providing a target DNA; (b) annealing at least one inosine-containing primer to the target DNA to create a target DNA:primer hybrid; (c) combining the target DNA:primer hybrid with a nuclease, which is capable of nicking DNA 3' to an inosine residue; and (d) adding at least one DNA polymerase and a dNTP mixture to the DNA:primer hybrid mixture and allowing the combination to act repeatedly initiating strand displacement synthesis thereby producing additional complementary copies of the target DNA strand. In some embodiments, steps (a)-(d) may occur substantially simultaneously. In alternative embodiments, step (b) may occur before step (c). In some embodiments, all of steps (a)-(d) occur within a temperature range of 1° C., 5° C., or 10° C.

In some embodiments multiple paired forward and reverse inosine-containing primers are annealed to the target DNA. The multiple paired multiple primers may optionally include at least one extender template. In some primers, the inosine may be positioned at least 4 nucleotides from the 5' end of the primer. The inosine-containing primer may be 5 to 100 nucleotides in length, 5 to 30 nucleotides in length, or 5 to 20 nucleotides in length. In some embodiments the inosine-containing primer may demonstrate a melting temperature of 25° C. to 70° C., 30° C. to 65° C., or 40° C. to 55° C. in the reaction mixture. In some embodiments, the inosine-containing primer demonstrates a melting temperature of 45° C. in the reaction mixture.

In some embodiments the nuclease may be an endonuclease V, for example, E. coli endonuclease V, A. fulgidus Endonuclease V, or T. maritime endonuclease V. In some embodiments, the endonuclease V may be from a protein the sequence of which consists of SEQ ID NO.:1, SEQ ID NO.:2, SEQ ID NO.:3, or conservative variants thereof.

The dNTP mixture may consist of dTTP, dGTP, dATP, and dCTP, or analogs thereof, which are each present in the reaction mixture at a final concentration of 10 μM to 20,000 μM, 100 μM to 1000 μM, or 200 μM to 300 μM.

In some embodiments, the methods of producing an amplicon may further comprise the step of denaturing (e.g., chemically or thermally) the target DNA prior to the annealing step. In embodiments where the target DNA is chemically denatured, glycerol, ethylene glycol, or formamide at a final concentration of 1% (vol./vol.) to 25% (vol./vol.) may be employed. In embodiments where the target DNA is thermally denatured the denaturing step comprises thermally denaturing the target DNA (e.g., by heating the target DNA at 95° C.).

The reaction mixture may further include a buffer selected from Tris, HEPES, or MOPS. In some embodiments, the reaction mixture further comprises a surfactant selected from Tween-20, NP-40, Triton-X-100, or a combination thereof. In yet other embodiments, the reaction mixture may include a divalent cation selected from $Mn^{+2}$, $Mg^{+2}$, or a combination thereof, which may be present in the reaction mixture at a final concentration of 2 mM to 6 mM.

The reaction mixture may further include a reducing agent (e.g., dithiothreitol (DTT), 2-mercaptoethanol βME), 2-mercaptoethylamine (MEA), or Tris(carboxyethyl)phosphine (TCEP)). In some embodiments, the reaction mixture may include at least one single stranded DNA binding protein (e.g., E. coli SSB, T4 gene 32 protein, T7 gene 2.5 protein, Ncp7, recA, or combinations thereof). In some embodiments, at least one single stranded DNA binding protein may be present in the reaction mixture at a final concentration of at least 0.1 ng/microliter.

In some embodiments, the reaction mixture may also include at least one blocking agent comprising albumin (e.g., BSA or HSA). In some other embodiments reaction mixture may include at least one topoisomerase (e.g., a type 1 topoisomerase). In some embodiments, the topoisomerase may be present in the reaction mixture at a final concentration of at least 0.1 ng/microliter. In all embodiments, the target DNA is of eukaryotic origin, prokaryotic origin, viral origin, bacteriophage origin, or synthetic origin.

Also provided herein are amplicon production kits, which may comprise: at least one inosine-containing primer; at least one DNA polymerase (e.g., exonuclease deficient T7 DNA polymerase, Bst DNA polymerase, exo (−) Klenow, delta Tts DNA polymerase, or combinations thereof); a buffer (e.g., Tris, HEPES, or MOPS); a dNTP mixture (e.g., a combination of dTTP, dGTP, dATP, and dCTP, or analogs thereof); and at least one nuclease that is capable of nicking DNA at a residue 3' to an inosine residue (e.g., an endonuclease V). In some embodiments, the endonuclease V is selected from a protein the sequence of which consists of SEQ ID NO.:1, SEQ ID NO.: 2, SEQ ID NO.: 3, or conservative variants thereof.

In some embodiments, at least one inosine-containing primer comprises multiple paired forward and reverse inosine-containing primers, which optionally may include at least one extender template. In some embodiments, the inosine is positioned at least 4 nucleotides from the 5' end of the inosine-containing primer. In some embodiments, the inosine-containing primer is 5 to 100 nucleotides in length, 5 to 30 nucleotides in length, or 5 to 20 nucleotides in length. In still other embodiments, the inosine-containing primer demonstrates a melting temperature of 25° C. to 70° C., 30° C. to 65° C., or 40° C. to 55° C.

In some embodiments, the amplicon production kit may further comprise a chemical denaturant (e.g., glycerol, ethylene glycol, or formamide). In yet other embodiments, the buffer may include a surfactant (e.g., Tween-20, NP-40, Triton-X-100, or a combination thereof). In some embodiments the amplicon production kit may further include one or more divalent cations (e.g., $Mn^{+2}$, $Mg^{+2}$, or a combination thereof), which may be present in the buffer at a final concentration of 2 mM to 6 mM. In some embodiments, the amplicon production kit of claim may further comprise a reducing agent (e.g., dithiothreitol (DTT), 2-mercaptoethanol (βME), 2-mercaptoethylamine (MEA), or Tris(carboxyethyl)phosphine (TCEP).

In some embodiments, the amplicon production kit may further comprise at least one single stranded DNA binding protein (e.g., E. coli SSB, T4 gene 32 protein, T7 gene 2.5 protein, Ncp7, recA, or combinations thereof).

In yet other embodiments, the amplicon production kit further comprises at least one at least one blocking agent comprising albumin and/or at least one topoisomerase.

FIGURES

These and other features, aspects, and advantages of the present invention will become better understood when the following detailed description is read with reference to the accompanying figures wherein:

FIG. 1 shows a general scheme for inosine-based amplicon production.

FIG. 2 depicts several synthesis schemes presented as a single series. The synthesis schemes shown in FIG. 2 provide methods for generating plus strands from a target DNA using a forward primer; generating minus strands using a reverse primer; addition of a promoter to the DNA product using an extender template; and generating RNA products using an RNA polymerase capable of initiating synthesis at the promoter that was added with the extender template.

FIG. 6 depicts in vitro translation, variations in divalent cation, and variations in single strand binding proteins described in Example 5 below.

Figure 12:
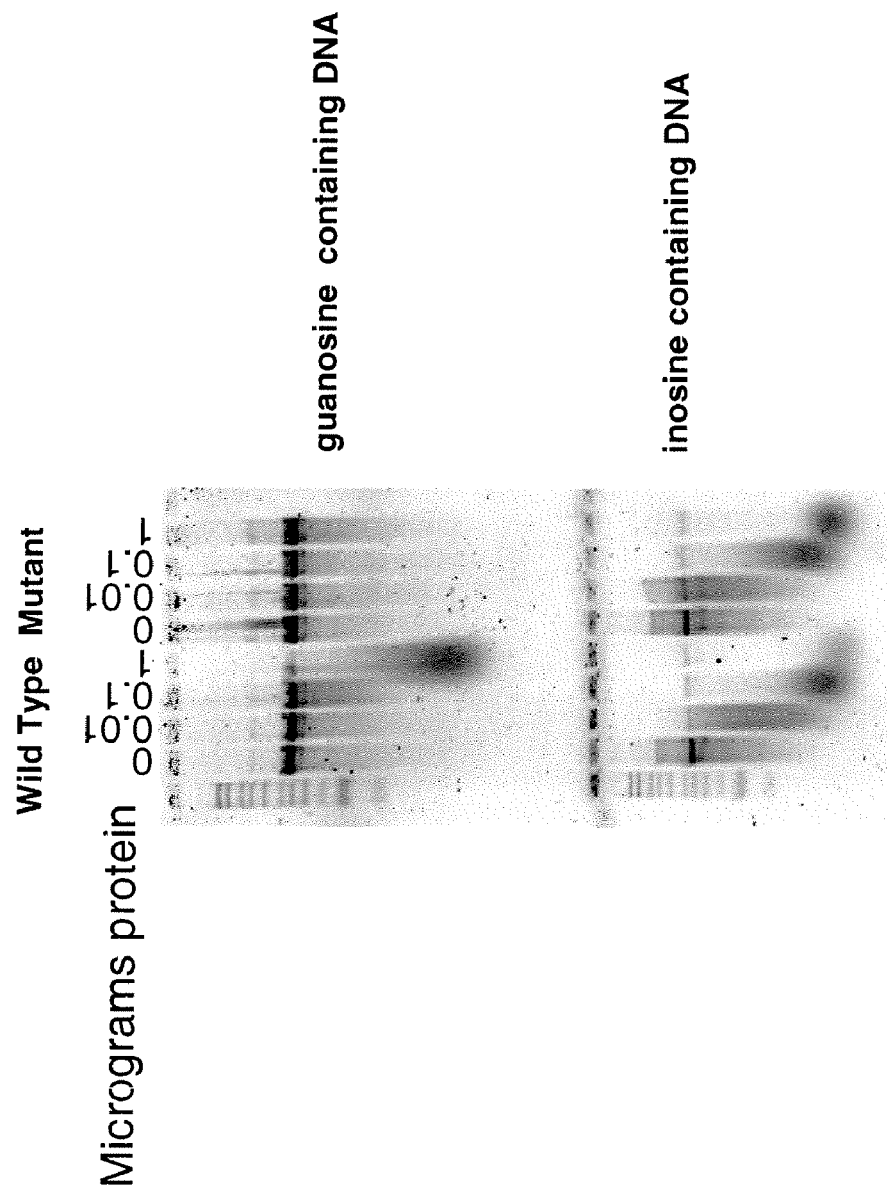

FIG. 12 demonstrates that both WT and mutant endonuclease V nucleases act on inosine-containing DNA but substantially not on the guanine-containing DNA as described in Example 13.

Figure 13:
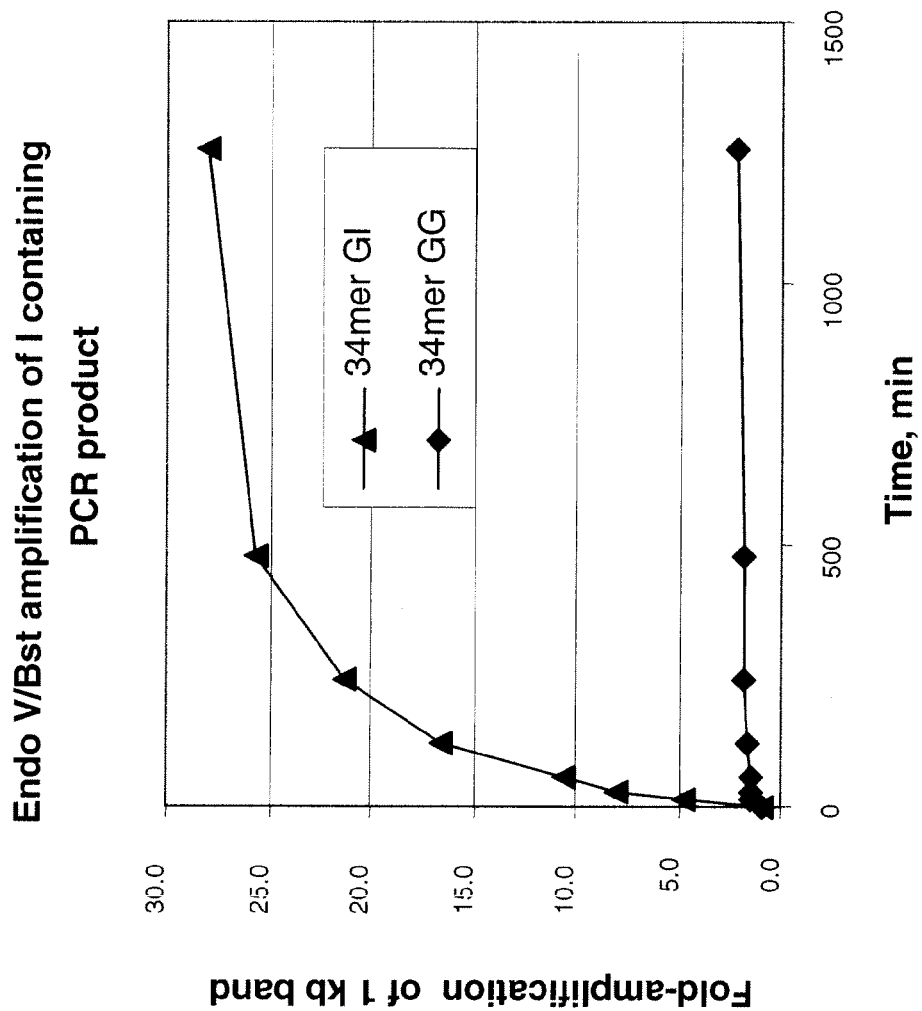

FIG. 13 demonstrates that the nuclease/polymerase combination generates amplicon DNA from inosine-containing DNA but not on the guanine-containing DNA as described in the Example 14.

Figure 14:
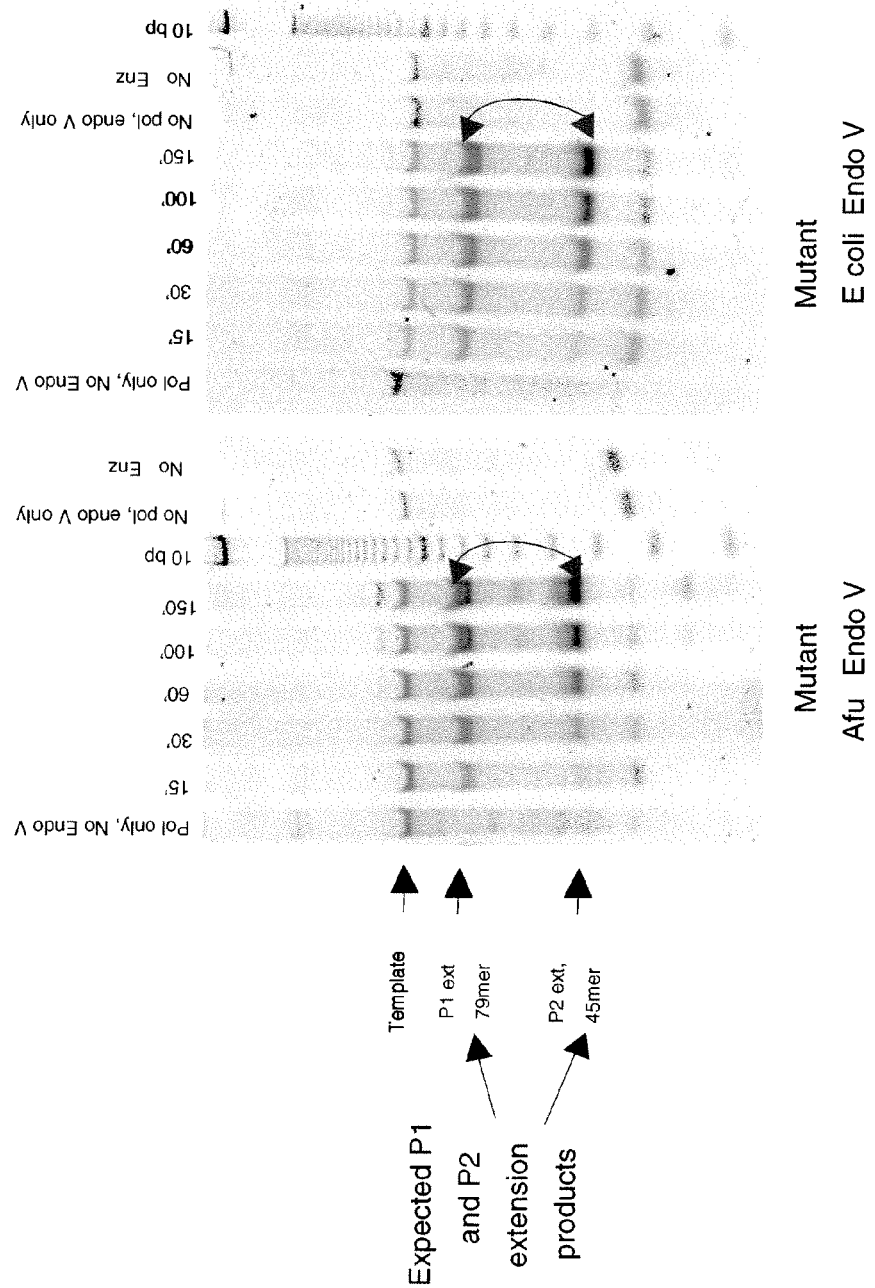

FIG. 14 depicts the results of a series of experiments that demonstrate the ability of the Y75A Archaeoglobus fulgidus ("Afu") endonuclease V variant (SEQ ID NO.:3) and the E. coli endonuclease V variant (SEQ ID NO.:2) to function with polymerase to generate amplicons from target DNA as described in Example 15.

Figure 15:
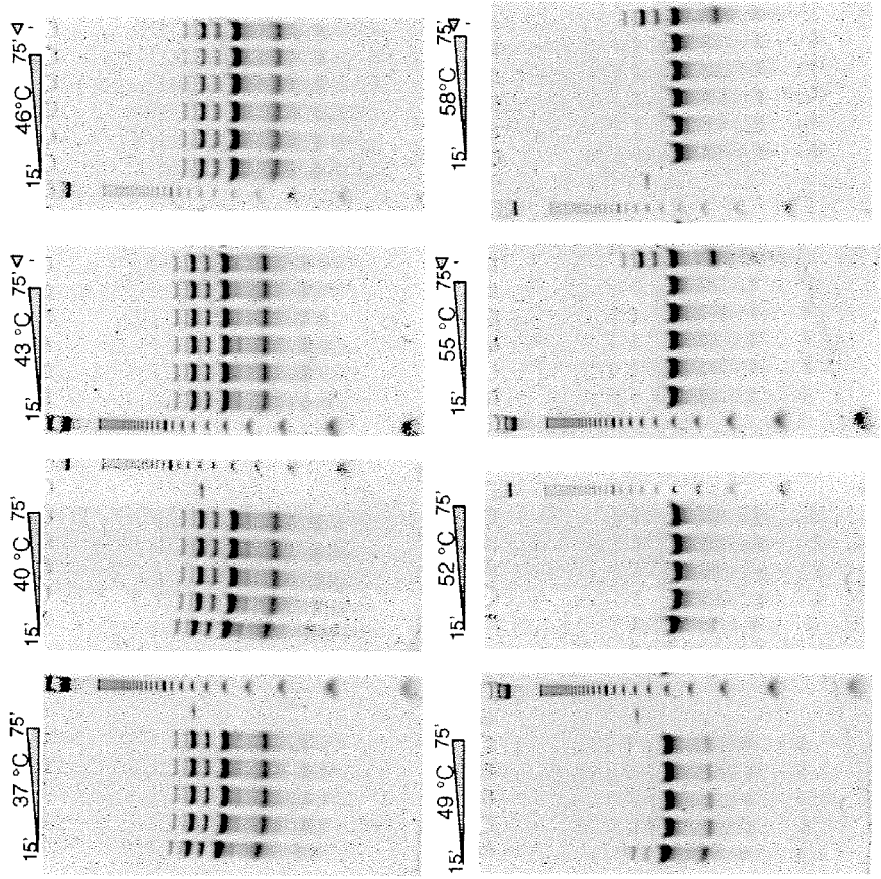

FIG. 15 shows the thermal stability of the Y75A E. coli endonuclease V variant (SEQ ID NO.:3) at a variety of temperatures as described in Example 16.

Figure 16:
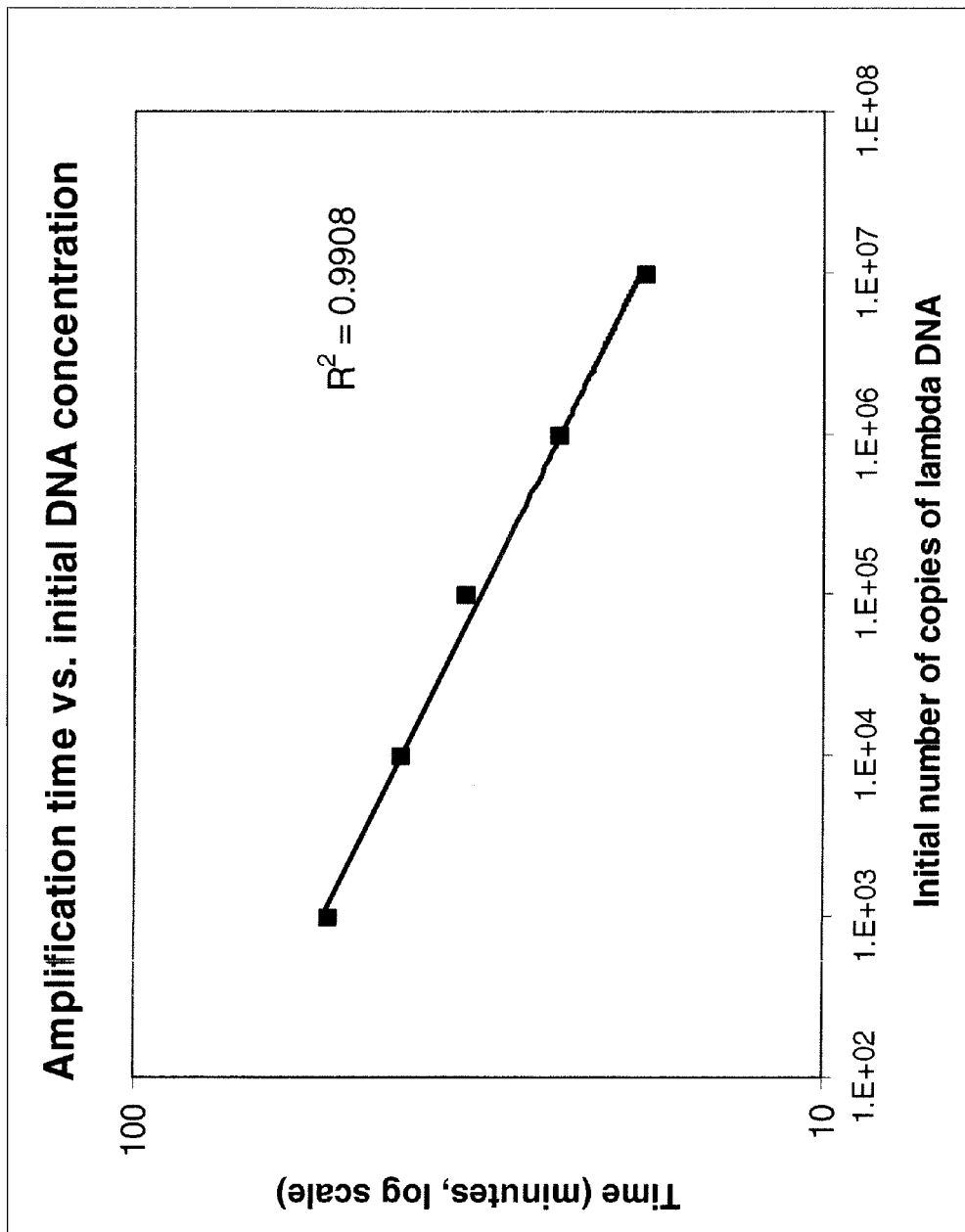

FIG. 16 shows the results of real-time DNA amplification as described in Example 17.

DETAILED DESCRIPTION

The following detailed description is exemplary and not intended to limit the invention of the application and uses of the invention. Furthermore, there is no intention to be limited by any theory presented in the preceding background of the invention of the following detailed description of the figures.

To more clearly and concisely describe and point out the subject matter of the claimed invention, the following definitions are provided for specific terms that are used in the following description and the claims appended hereto.

The term "amplicon" generally refers to a DNA amplification product containing one or more target DNA sequences that result from the amplification of a target DNA driven by endonuclease nicking of an inosine-containing primer coupled with polymerase extension. Amplicons may be generated using a single inosine-containing primer, paired inosine-containing primers, or nested-paired inosine-containing primers. An amplicon may comprise single-stranded or double-stranded DNA, DNA:RNA hybrids, or RNA.

Amplicons may comprise a mixture of amplification products (i.e., a mixed amplicon population), several dominant species of amplification products (i.e., multiple, discrete amplicons), or a single dominant species of amplification product. In some embodiments, a single species of amplicon may be isolated from a mixed population using art-recognized techniques, such as affinity purification or electrophoresis. An amplicon may be largely single-stranded or partially or completely double-stranded DNA, DNA:RNA hybrids, or RNA depending on the reaction scheme used.

"Biological sample" as used herein refers to a sample obtained from a biological subject that contains or is suspected of containing target nucleic acids. A biological sample also includes samples from a region of a biological subject containing diseased cells. A biological sample may be of eukaryotic origin, for example, insects, protozoa, birds, fish, reptiles, and preferably a mammal, for example, rat, mouse, cow, dog, guinea pig, or rabbit, or a primate, for example, chimpanzees or humans. Alternatively, a biological sample may be of prokaryotic origin or viral or bacteriophage origin.

The term "conservative variants" as used herein applies to both amino acid and nucleic acid sequences. With respect to particular nucleic acid sequences, the term "conservative variants" refers to those nucleic acids that encode identical or similar amino acid sequences and include degenerate sequences. For example, the codons GCA, GCC, GCG, and GCU all encode alanine. Thus, at every amino acid position where an alanine is specified, any of these codons may be used interchangeably in constructing a corresponding nucleotide sequence. Such nucleic acid variants are conservative variants, since they encode the same protein (assuming that is the only alternation in the sequence). One skilled in the art recognizes that each codon in a nucleic acid, except for AUG (sole codon for methionine) and UGG (tryptophan), may be modified conservatively to yield a functionally identical peptide or protein molecule. As to amino acid sequences, one skilled in the art will recognize that substitutions, deletions, or additions to a polypeptide or protein sequence which alter, add or delete a single amino acid or a small number (typically less than about ten) of amino acids is a "conservative variant" where the alteration results in the substitution of one amino acid with a chemically similar amino acid.

The term "complementary," as used herein, refers to the capacity for precise pairing between nucleotides within an oligonucleotide or polynucleotide. For example, A (adenosine) pairs with T (thymine) and G (guanosine) pairs with C (cytosine) by hydrogen bonding. If a nucleotide at a certain position of an oligonucleotide is capable of hydrogen bonding with a nucleotide at a corresponding position within a DNA molecule, then the oligonucleotide and the DNA are considered to be complementary to each other at that position. The whole oligonucleotide and the DNA are considered complementary to each other when a sufficient number of corresponding positions in each have nucleotides that hydrogen bond with each other.

As used herein, the term "dNTP mixture" generally refers to a combination of deoxynucleotides containing a phosphate, sugar and organic base in the triphosphate form, that provide precursors required by a DNA polymerase for DNA synthesis. A dNTP mixture may include each of the naturally occurring deoxynucleotides (i.e., adenine (A), guanine (G), cytosine (C), uracil (U), and Thymine (T)). In some embodiments, each of the naturally occurring deoxynucleotides may be replaced or supplemented with a synthetic analog; provided however that inosine may not replace or supplement G in a dNTP mixture.

As used herein the term "inosine" refers to a 2'-deoxyribonucleoside or ribonucleoside having an analog of the normal bases, particularly the deaminated or similar bases recognized and cleaved by endonuclease V when encountered in DNA. As used herein the term "inosine analog" refers to a 2'-deoxyribonucleoside or ribonucleoside wherein the base includes, for example, hypoxanthine (i.e., inosine proper), xanthine, uridine, oxanine (oxanosine), other O-1 purine analogs, N-6-hydroxylaminopurine, nebularine, 7-deaza hypoxanthine, other 7-deazapurines, and 2-methyl purines.

As used herein the term "inosine containing primer" refers to a primer including at least one inosine or inosine analog.

A "purified" or "isolated" polypeptide or polynucleotide is one that is substantially free of the materials with which it is associated in nature. By substantially free is meant at least 50%, preferably at least 70%, more preferably at least 80%, even more preferably at least 90% free of the materials with which it is associated in nature.

As used herein the term "primer" generally refers to a linear oligonucleotide that is complementary to and anneals to a target sequence. The lower limit on primer length is determined by ability to hybridize since very short primers (less than 5 nucleotides long) do not form thermodynamically stable duplexes under most hybridization conditions. Primers may vary in length from 8 to 50 nucleotides. In some embodiments the primer ranges in length from 15 nucleotides to 25 nucleotides. Suitable primers include at least one inosine positioned near the 3' end of the primer (e.g., at penultimate nucleotide of the 3' end of the primer). As used herein the term "forward primer" refers to a primer that includes an inosine at the penultimate 3' position, which anneals to one particular strand of the target DNA. As used herein the term "reverse primer" refers to a primer that includes an inosine at the penultimate 3' position that anneals to the opposite strand of the target. Together a forward primer and a reverse primer are generally oriented on the target DNA sequence in a manner analogous to PCR primers, so that their 3' ends are both closer to the target sequence than their 5' ends. Both naturally occurring (G, A, C, and T) and analog nucleotides are useful as component nucleotides for primers.

As used herein the term "melting temperature" with respect to a primer refers to the temperature at which 50% of primer-DNA hybrids dissociate into free primer and DNA. The melting temperature of a primer increases with its length. The melting temperature of a primer can also depend on its nucleotide composition. Thus primers with many G and C nucleotides will melt at a higher temperature than ones that only have A and T nucleotides. High melting temperatures (e.g., above 65° C.) and very high melting temperatures (e.g., above 80° C.), may be disfavored in certain embodiments because some DNA polymerases denature and lose activity at high temperatures. Because ionic strength also affects the melting temperature of a primer, all melting temperature values provided herein are determined at a pH of 7.7 with 5 mM $MgCl_2$ and 50 mM NaCl.

As used herein, the terms "reducing agent" and "reducing agents" refer to agents that reduce disulfides to mercaptans. Suitable reducing agents may contain thiol groups such as dithiothreitol (DTT), 2-mercaptoethanol (βME), and 2-mercaptoethylamine (MEA). Alternatively, reducing agents may contain phosphines and their derivatives, for example Tris (carboxyethyl)phosphine (TCEP).

As used herein the term "single strand DNA binding protein" abbreviated as "ssb" refers to proteins that bind noncovalently to single stranded DNA with a higher affinity than to double stranded DNA. Suitable examples of single strand binding proteins include, but are not limited to, *E. coli* SSB, T4 gene 32 protein, T7 gene 2.5 protein, Ncp7, recA, or combinations thereof.

As used herein the term "target DNA" refers to a DNA sequence region of natural or synthetic origin that may be synthesized or amplified using one of more of the methods of the present invention.

As used herein, the term "template" refers to the portion of the target DNA used by DNA polymerase produce one or more amplicons.

As used herein, the term "transformed cell" means a cell into which (or into predecessor or an ancestor of which) a nucleic acid molecule encoding a polypeptide of the invention has been introduced, by means of, for example, recombinant DNA techniques or viruses.

The term "vector" refers to any autonomously replicating or integrating agent, including but not limited to plasmids, cosmids, and viruses (including phage), comprising a nucleic acid molecule to which one or more additional nucleic acid molecules may be added. Included in the definition of "Vector" is the term "expression vector." Vectors may be used both to amplify and to express DNA (e.g., genomic or cDNA) or RNA.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EMBODIMENTS

Provided herein are methods for synthesizing nucleic acid sequences by introducing an inosine into a specific position of a target DNA using, for example, an oligonucleotide primer, followed by application of a polymerase and an endonuclease V to nick the DNA and a polymerase to repeatedly make the compliment of the target DNA strand. The inosine nucleotide may be positioned at least 4 nucleotides, at least 5 nucleotides, or at least 10 nucleotides from the 5' end of the primer, substituting for a guanosine and opposite a cytosine. In certain embodiments, the inosine nucleotide may be the penultimate 3' nucleotide of the primer. In alternative embodiments, inosine may be present at both the penultimate 3' residue and ultimate 3' residue.

The invention involves the synthesis of DNA using DNA polymerase. DNA polymerases use nucleoside triphosphates to add nucleotides to the 3' end of a primer based on a template strand of DNA in a complementary fashion, creating a new DNA strand complementary to the original. The product may be single stranded or double-stranded DNA, often extending to the end of the template strand. Endonuclease V is a nuclease that specifically nicks DNA two nucleotides 3' of an inosine nucleotide, when the target DNA is double stranded the nick occurs in the same strand as the inosine. The endonuclease, in combination with a strand displacing DNA polymerase and a primer produces targeted DNA amplification. First, the DNA polymerase extends the primer, creating a nicking site for the nuclease. Nicking creates an initiation site for the DNA polymerase, displacing a single-stranded DNA product while it re-creates the double-stranded primer extension product. The cycle repeats, synthesizing multiple single strands of DNA complementary to the downstream portion of the template.

With a single, forward primer, the rate of synthesis of complimentary copies of each molecule is relatively constant, resulting in a steady, linear increase in the number of copies with time. When second primer in the reverse direction is added anneals to the target DNA at a defined distance from the forward primer, amplification process is accelerated. The forward and reverse primers may be placed relatively close to each other (i.e., less than about 1 kb apart), minimizing the time required to copy the forward amplicon to its 5' end as defined by the endonuclease V cleavage site, thereby increasing the relation and reducing the total time required to generate amplicons from the target DNA. The reaction rate reaches a maximum when the amount of nuclease or polymerase of other component becomes limiting. Additional pairs of nested primer may also be used to further increase amplification rates.

Reaction temperatures may vary during the amplicon production process ranging from 1° C., 5° C., or 10° C. In some particularly preferred embodiments the reaction temperature may be held at 46° C.

In alternative embodiments, using extender templates, which are specific sequences (e.g., a promoter sequence or a restriction endonuclease site specific sequence) may be annealed at the 3' end of the amplicon by incorporating in an inosine-containing primer. An extender template may be designed so that the 3' end of the amplicon will anneal to it. If the extender template contains two stretches of sequence, one complementary to the amplicon, and one that is not, and hybridization creates a 5' overhang of the non-complementary primer sequence, the 3' recessed end of the amplicon will be further extended by the DNA polymerase. This extension reaction may be employed to incorporate specific DNA sequences at the 3' end of the innermost amplicon.

The 5' end of the extender template may contain a hairpin loop, with a fluorescent dye and a quencher located on either arm of the stem, then the dye fluorescence may be largely quenched by energy transfer. Upon extension by the strand displacing DNA polymerase from the recessed 3' end of the amplicon, the stem-loop structure will become double stranded and the dye and quencher, will become further separated, eliminating some or all of the quenching, and generating a detectable signal. This signal may be multiplexed by the sequence of the extender template and the color of the quenched dye so that 2 or more independent amplification processes may be monitored simultaneously.

In some embodiments the 5' end of the extender template may include the complement of an RNA polymerase promoter sequence. Thus, a double stranded RNA polymerase promoter may be generated by hybridization of extender template to the amplicon followed by extension by the DNA polymerase of the 3' end of the amplicon into the promoter region. In embodiments where an RNA polymerase is included in the reaction, the amplicon may be transcribed as a single-stranded RNA polymerase template. In all embodiments, the nucleic acids produced by the present methods may be determined qualitatively or quantitatively.

In embodiments where terminal-phosphate-labeled ribonucleotides are used, the phosphatase may be used for color generation in a qualitative or quantitative assay. In such embodiments, the terminal phosphate may be protected from dephosphorylation by using terminal-phosphate methyl esters of dNTP's or deoxynucleoside tetraphosphates.

Samples suspected or known to contain a particular target nucleic acid sequence may be obtained from a variety of sources. The sample may be, for example, a biological sample, a food, an agricultural sample, or an environmental sample. Samples may also be derived from a variety of biological subjects. The biological subject may be of prokaryotic or eukaryotic origin and includes viruses. Such samples derived from a biological subject may be derived from biological tissue or body fluid or exudate (e.g., blood, plasma, serum or urine, milk, cerebrospinal fluid, pleural fluid, lymph, tears, sputum, saliva, stool, lung aspirates, throat or genital swabs, and the like), whole cells, cell fractions, or cultures.

Target nucleic acid in the sample may be dispersed in solution or may be immobilized on a solid support (such as blots, arrays, microtiter, or well plates). A sample may be pretreated make the target nucleic acid available for hybridization. When the target nucleic acid is present in double stranded form, may optionally be denatured to generate single stranded form.

Endonuclease V (also called endo V or inosine 3' endonuclease) is an *E. coli* repair enzyme that recognizes DNA containing inosines and hydrolyzes the second or third phosphodiester bonds 3' to the inosine, leaving a nick with 3'-hydroxyl and 5'-phosphate. In some embodiments, wild type endonuclease V (e.g., SEQ ID NO.:1) may be employed in the inventive methods. In alternative embodiments, the variants provided herein as SEQ ID NO.:2 or SEQ ID NO.:3 may be used to nick the inosine-containing target DNA.

In embodiments where the target DNA is partially or fully heat denatured, heat stable endonuclease V variants are preferred. In embodiments where the target DNA is not heat denatured, endonuclease V variants that have maximum activity at a relatively low temperature (e.g., 45° C.) may be preferred.

DNA polymerases suitable for use in the inventive methods may demonstrate one or more of the following characteristics: strand displacement activity; the ability to initiate strand displacement from a nick; and low degradation activity for single stranded DNA. Exemplary DNA polymerases useful for the methods include, without limitation, Bst DNA polymerase, exo (−) Klenow, and delta Tts DNA polymerase.

Nucleotides useful in the inventive methods include both deoxyribonucleotides ("dNTPs") and ribonucleotides ("rNTPs"). The dNTP mixture provides a combination of deoxynucleotides required by a DNA polymerase for DNA synthesis. The dNTP mixture may include each of the naturally occurring deoxynucleotide bases (i.e., adenine (A), guanine (G), cytosine (C), and Thymine (T)). In some embodiments, each of the naturally occurring deoxynucleotides may be replaced or supplemented with a synthetic analog; provided however that deoxyinosinetriphosphate may not replace or supplement dGTP in the dNTP mixture In some embodiments, the synthesis reactions take place in a buffer that results in a reaction pH of between 6 and 9. In some preferred embodiments, the pH is 7.7. Most art-recognized buffers for nucleic acid synthesis reactions (e.g., Tris buffers or HEPES buffers) may be employed.

In general, buffers that enhance DNA stability (e.g., HEPES) may be preferred in certain amplicon production methods. However, Tris:Borate, HEPES, and MOPS buffers may be disfavored for some specific amplicon production methods employing thermal denaturation of a target DNA.

Polymerase enzymes typically require divalent cations (e.g., $Mg^{+2}$, $Mn^{+2}$, or combinations thereof). Accordingly, in certain embodiments, one or more divalent cations may be added to the reaction mixture. $MgCl_2$ may be added to the reaction mixture at a concentration range of 2 mM to 6 mM. Higher concentrations of $MgCl_2$ are preferred when high concentrations (e.g., greater than 10 pmoles, greater than 20 pmoles, or greater than 30 pmoles) of inosine-containing primer or primers are added to the reaction mixture.

Surfactants (e.g., detergents) may be added to the reaction mixture. In some embodiments, the surfactant is a detergent selected from Tween-20, NP-40, Triton-X-100, or combinations thereof. In some preferred embodiments, 0.05% NP-40 and 0.005% Triton X-100 are added to the reaction mixture. Surfactants may be applied to the reaction tube before introducing the first component of the reaction mixture. Alternatively, surfactants may be added to the reaction mixture along with the reaction components. In some specific embodiments, the reaction buffer may comprise 25 mM Tris:borate; 5 mM $MgCl_2$; 0.01% Tween; and 20% ethylene glycol.

One or more blocking agents such as an albumin (e.g., BSA) may be added to the reaction mixture to bind to the surface of the reaction vessel (e.g., plastic microcentrifuge tube or microtiter plate) increasing the relative amount target DNA that is available for reaction with the nucleases or polymerases.

One or more reducing agents (e.g., DTT, βME, TCEP, or MEA) may be added to the reaction mixture to reduce oxidation of the enzymes in the reaction mix and improve the quality and yield of the amplicons produced.

The target dsDNA may be thermally denatured, chemically denatured, or both thermally and chemically denatured. In certain embodiments, the temperature does not substantially change during the various reaction steps (e.g., 1° C., 5° C., or 10° C.).

In some embodiments, the dsDNA is chemically denatured using an denaturant (e.g., glycerol, ethylene glycol, formamide, or a combination thereof) that reduces the melting temperature of dsDNA. In certain embodiments, the denaturant reduces the melting temperature 5° C. to 6° C. for every 10% (vol./vol.) of the denaturant added to the reaction mixture. The denaturant or combination of denaturants may comprise 5%, 10% (vol./vol.), 15% (vol./vol.), 20% (vol./vol.), or 25% (vol./vol.) of reaction mixture.

In certain embodiments, the denaturant comprises ethylene glycol. In alternative embodiments, the denaturant is a combination of glycerol (e.g., 10%) and ethylene glycol (e.g., 6% to 7%).

Salts that reduce hybridization stringency may be the reaction buffers at low concentrations for embodiments wherein target DNA is chemically denatured at low temperatures.

Inosine-containing primers may be synthesized using art-recognized synthesis techniques. Primer design software (e.g., "autodimer") may be employed to design a single primer or multiple primers capable of annealing to a nucleic acid and facilitating polymerase extension. In embodiments where the reaction proceeds at temperatures in the range of 1° C., 5° C., or 10° C., the melting temperature of the primer is preferably 45° C. in approximately 50 mM salt. In some embodiments, relatively short primers (e.g., 10-mers to 20-mers; more preferably 14-mers to 18-mers, most preferably 16-mers) may be employed.

In some preferred embodiments, the inosine-containing primer is designed such that the inosine residue is positioned in the primer at a location complementary to a C in the target DNA. In some embodiments, the inosine appears as the penultimate 3' base of the primer. Because the reaction conditions (i.e., temperature and ionic strength) effect annealing of primer to target DNA, optimal positioning of the inosine in the prime may be adjusted according to the reaction conditions. In general, the inosine residue is positioned away from the 5' end of the prime such that the primer remains annealed to the target DNA after nicking by the endonuclease. Accordingly, the segment of the primer 5' of the inosine should have a melting temperature approximately equal to the reaction temperature at the chosen reaction conditions. If there are two template G's in a row, two inosines may appear in the primer as the both the penultimate 3' and the final 3' residues.

Multiple primers may be included in the reaction mixture in some embodiments. Embodiments where both the plus and minus strands are generated, at paired primers comprising a forward primer and a reverse primer may be included in the reaction mixture. The inclusion of multiple paired primers may improve the relative percentage of a discrete product in the reaction mixture. Nested primers may be designed to bind at or near the 3' end of the previous amplicon so that in a series, each primer in the series will hybridize next to each other on the original target. Where multiple nested primers are used, SSB (from 1 ng to 1 μg in a 10 μL volume) may be included in the reaction mixture to increase fidelity and reduce background.

Figure 1:
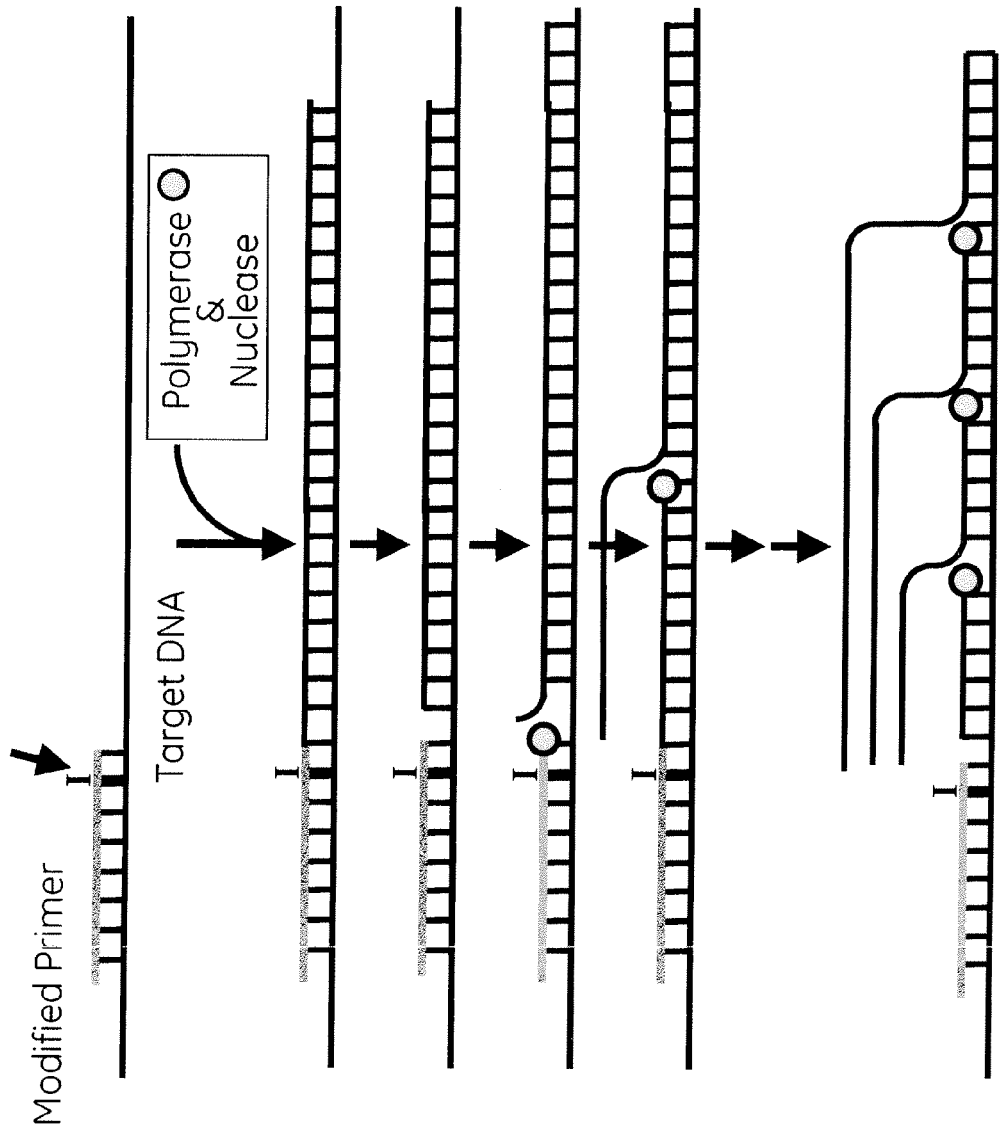
Figure 2:
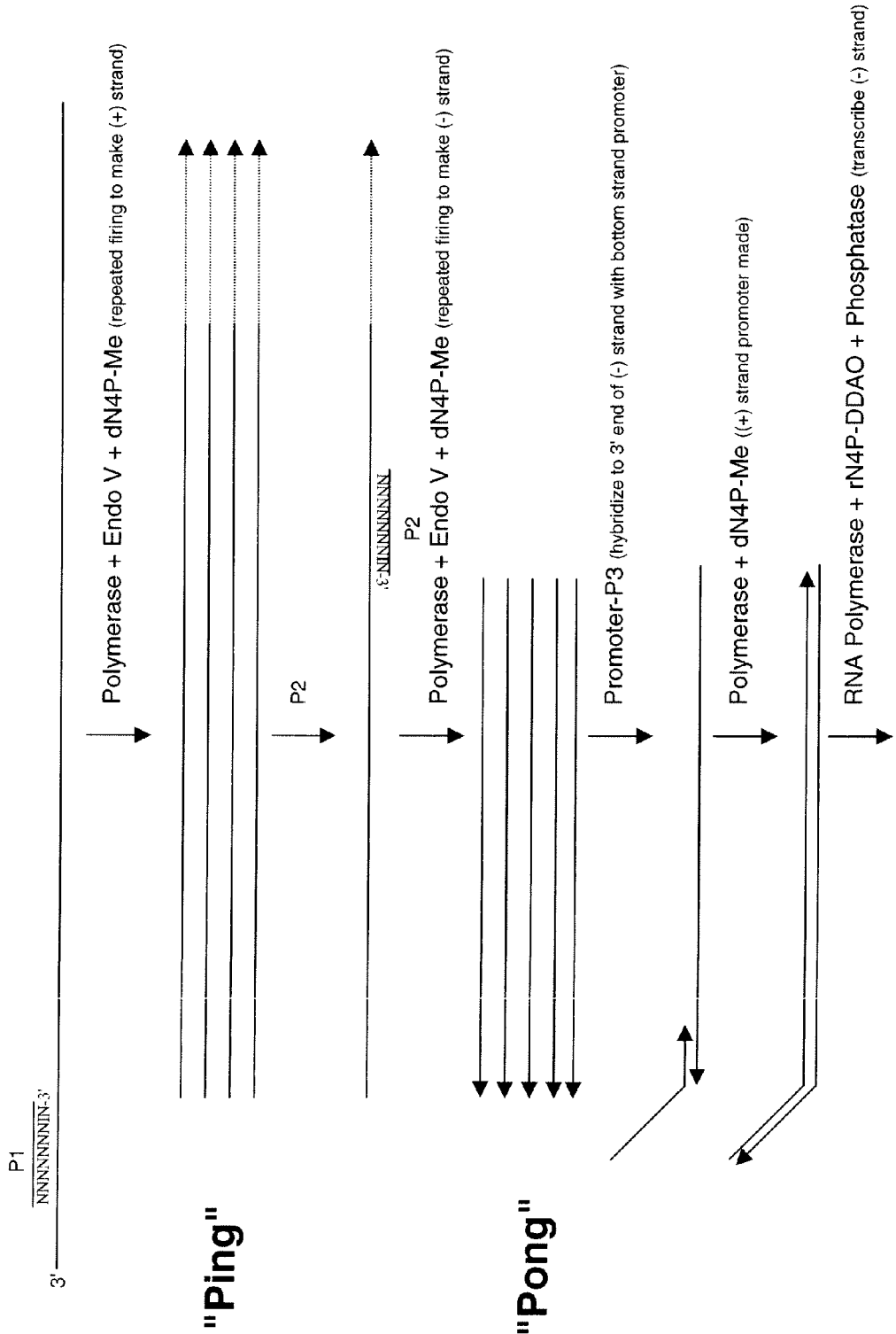
Figure 3:
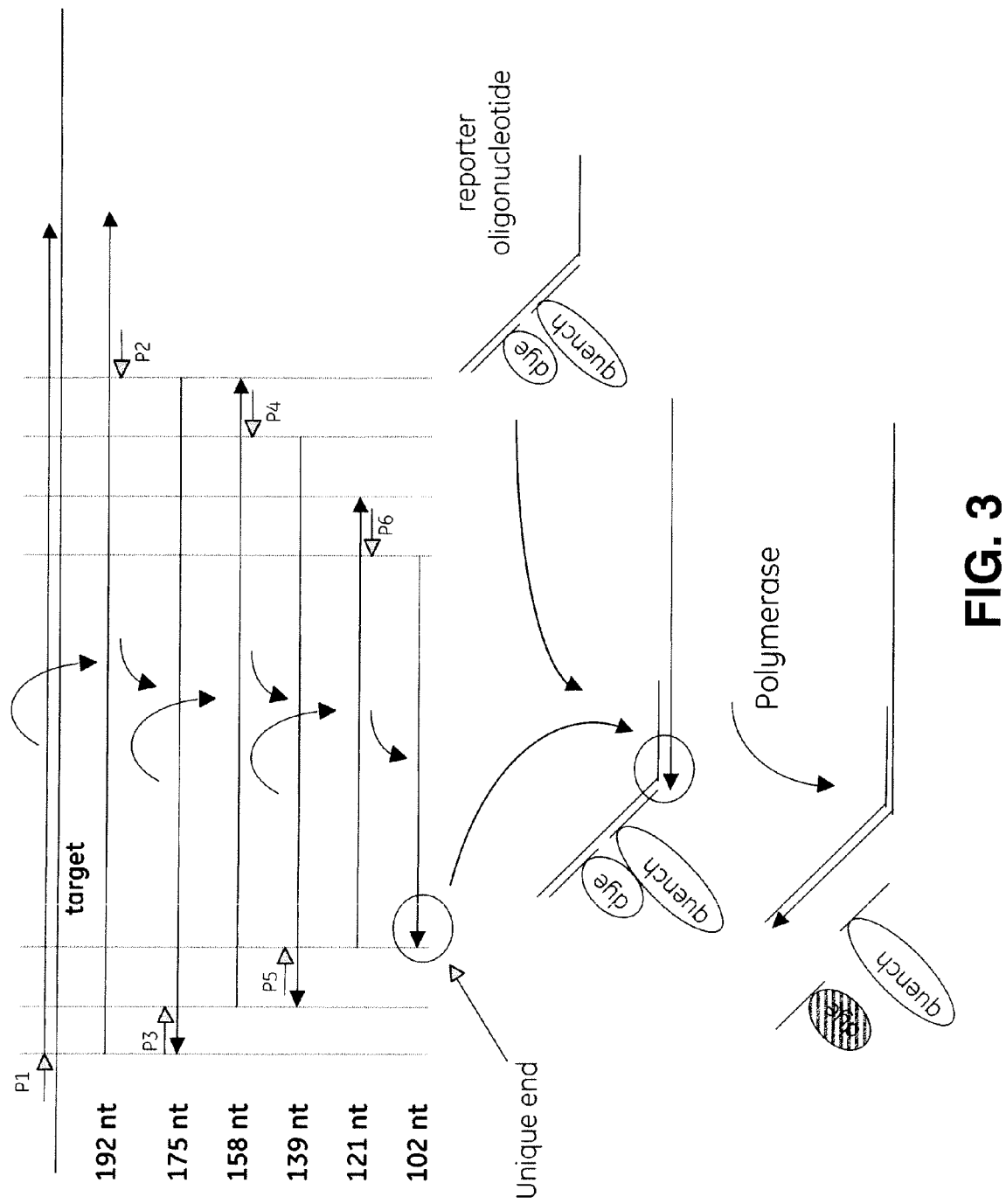
FIG. 3 shows a general scheme for detecting amplicons using paired fluorescent and quenching chromophores attached to oligonucleotides connected by hybridization to an extender template.

The basic method shown in FIG. 1 may be varied by employing additional primers or other oligonucleotides, additional enzymes, additional nucleotides, stains, dyes, or other labeled components. Thus, for example, amplification with a single primer may be used for dideoxy sequencing, producing multiple sequencing products for each molecule of template, and, optionally by the addition of dye-labeled dideoxynucleotide terminators. Labeled probes may be generated from double-stranded cDNA made with a sequence-tagged oligo dT primer from mRNA samples. A single primer may be the complement of the tag sequence, facilitating identification and/or isolation.

Amplification with multiple, paired primers facilitates rapid and extensive amplification, which is useful to detect the presence of specific sequences, to quantify the amounts of those sequences present in a sample, or to produce quantities of a sequence for analysis by methods such as electrophoresis for size measurement, restriction enzyme digestion, sequencing, hybridization, or other molecular biological techniques.

EXAMPLES

Practice of the invention will be still more fully understood from the following examples, which are presented herein for illustration only and should not be construed as limiting the invention in any way.

Commercially available stock buffers used in some of the Examples are shown in Tables 1-3 below. ThermoFidelase was obtained from Fidelity Systems, Gaithersburg, Md.; T7, DEPC water, and NaCl were obtained from Ambion, dNTPs were obtained from GE Healthcare; Tris-HCl and Tween 20 were obtained from Sigma Aldrich. (Volumes shown in the following Tables are in microliters unless otherwise indicated.)

10× Sequenase Buffer

TABLE 1

| Reagent | Vol. | [Conc.] |
| --- | --- | --- |
| 1 M Tris-HCl, pH 7.6 | 800 μL | 400 mM |
| 1 M MgCl2 | 400 μL | 200 mM |
| 5 M NaCl | 200 μL | 500 mM |
| 100 mM dATP | 50 μL | 2.5 mM |
| 100 mM dCTP | 50 μL | 2.5 mM |

TABLE 1-continued

| Reagent | Vol. | [Conc.] |
| --- | --- | --- |
| 100 mM dGTP | 50 μL | 2.5 mM |
| 100 mM dTTP | 50 μL | 2.5 mM |
| Tween 20 | 2 μL | 0.1% |
| 1 M DTT | 20 μL | 10 mM |
| DEPC Water | 378 μL | |
| Total Vol. | 2000 μL | |

10× Klenow Buffer

TABLE 2

| Reagent | Vol. | [Conc.] |
| --- | --- | --- |
| 1 M Tris-HCl, pH 7.6 | 1000 μL | 0.5 M |
| 1 M MgCl2 | 200 μL | 0.1 M |
| 100 mM dATP | 50 μL | 2.5 mM |
| 100 mM dCTP | 50 μL | 2.5 mM |
| 100 mM dGTP | 50 μL | 2.5 mM |
| 100 mM dTTP | 50 μL | 2.5 mM |
| Tween 20 | 2 μL | 0.1% |
| 1 M DTT | 20 μL | 10 mM |
| DEPC Water | 578 μL | |
| Total Volume | 2000 μL | |

10× Endonuclease V Buffer

TABLE 3

| |
| --- |
| 100 mM Tris-Borate pH 8 |
| 0.1% Tween 20 |
| 30 mM MgCl$_2$ |
| 2.5 mM each dNTP |
| 10 mM DTT |

Amplicons may be visualized and/or quantified using art-recognized techniques, for example, electrophoresis to separate species in the sample and observe using an intercalating dye (e.g., ethidium bromide, acridine orange, or proflavine). Amplicon production may also be tracked using optical methods (e.g., ABI Series 7500 Real-Time PCR machine) and an intercalating dye (e.g., SYBR Green I). The amplicons produced in the following examples were visualized using electrophoresis or optical techniques.

Table 4 provides the sequences of the endonuclease V variants, the template DNAs, and the various primers used in the examples that follow. *Bacillus cereus* strain ATCC 15816 DNA gyrase subunit A gene used as a template is identified as DNAG5 in the following examples.

TABLE 4

| | Ref No. | Sequence (N-term-C-term; 5'→3') | Length |
| --- | --- | --- | --- |
| WT *E. coli* endonuclease V | SEQ ID NO.: 1 | MDLASLRAQQIELASSVIREDRLDKDPPD LIAGADVGFEQGGEVTRAAMVLLKYPSLE LVEYKVARIATTMPYIPGFLSFREYPALL AAWEMLSQKPDLVFVDGHGISHPRRLGVA SHFGLLVDVPTIGVAKKRLCGKFEPLSSE PGALAPLMDKGEQLAWVWRSKARCNPLFI ATGHRVSVDSALAWVQRCMKGYRLPEPTR WADAVASERPAFVRYTANQP | 223 |
| GE *E. coli* i endonuclease V Y73A | SEQ ID NO.: 2 | MDLASLRAQQIELASSVIREDRLDKDPPD LIAGADVGFEQGGEVTRAAMVLLKYPSLE LVEYKVARIATTMPAIPGFLSFREYPALL AAWEMLSQKPDLVFVDGHGISHPRRLGVA SHFGLLVDVPTIGVAKKRLCGKFEPLSSE PGALAPLMDKGEQLAWVWRSKARCNPLFI ATGHRVSVDSALAWVQRCMKGYRLPEPTR WADAVASERPAFVRYTANQPLE | 225 |

TABLE 4-continued

| | Ref No. | Sequence (N-term-C-term; 5'→3') | Length |
|---|---|---|---|
| GE Afu endonuclease V | SEQ ID NO.: 3 | MLQMNLEELRRIQEEMSRSVVLEDLIPLE ELEYVVGVDQAFISDEVVSCAVKLTFPEL EVVDKAVRVEKVTFPAIPTFLMFREGEPA VNAVKGLVDDRAAIMVDGSGIAHPRRCGL ATYIALKLRKPTVGITKKRLFGEMVEVED GLWRLLDGSETIGYALKSCRRCKPIFISP GSYISPDSALELTRKCLKGYKLPEPIRIA DKLTKEVKRELTPTSKLK | 221 |
| Ban 1 Template | SEQ ID NO.: 4 | CAATTGTAATTTCTGTACGTCTCTTATCA TTGAAGCGCTCTTTTACTTCTGTTAATTC TTCACGAATAATCTCAAGA | 77 |
| P-1 | SEQ ID NO.: 5 | TCTTGAGATTATTCIT | 15 |
| P2-1 | SEQ ID NO.: 6 | CAATTGTAATTTCTIT | 15 |
| P3 | SEQ ID NO.: 7 | AAATTAATACGACTCACTATAGGGTGAAG AATTAACAGAAGTAAAAGAGCddC | 51 |
| P-3 Mismatched | SEQ ID NO.: 8 | AAATTAATACGACTCACTATAGGGTTGAA GAATTAACAGAAGTAAAAGAGA | 51 |
| P-3 NO ddC | SEQ ID NO.: 9 | AAATTAATACGACTCACTATAGGGTGAAG AATTAACAGAAG | 41 |
| P-3SD Mod | SEQ ID NO.: 10 | AAATTAATACGACTCACTATAGGGTTGAA GAATTAACAGAAGTAAAAGAGddC | 51 |
| Primer 1354 | SEQ ID NO.: 11 | TCGCTGAATTAAAAIC | 16 |
| Primer 1333 | SEQ ID NO.: 12 | ATCAAGATTTAATGAAIT | 18 |
| Primer 1498 | SEQ ID NO.: 13 | TGTTCTGGAATCAAIT | 16 |
| Primer 1517 | SEQ ID NO.: 14 | AACGTAATGGCGATIT | 16 |
| Primer 1275 | SEQ ID NO.: 15 | TTAGATATGCGTCTIC | 16 |
| Primer 1294 | SEQ ID NO.: 16 | GCTTAACAGGATTAIA | 16 |
| Primer 1313 | SEQ ID NO.: 17 | CGAAAAAATTGAACAAIA | 18 |
| Primer 1378 | SEQ ID NO.: 18 | CAGATGAAGAAAAGIT | 16 |
| Primer 1482 | SEQ ID NO.: 19 | CTTCATCTTCAATAIA | 16 |
| Primer 1534 | SEQ ID NO.: 20 | AATATAACCATTATGAIT | 18 |
| Primer 1560 | SEQ ID NO.: 21 | TACGTAGAAGCTGIC | 15 |
| Primer 1579 | SEQ ID NO.: 22 | ACCACGGTTCTGTIT | 15 |
| cP-3 3' Quencher | SEQ ID NO.: 23 | CCCTATAGTGAGTCGTATTAATTT-IowaBlack | 24 |
| Fluorescent Primer 1 | SEQ ID NO.: 24 | FAM-GGTCGACTIAGGAGGATCCCCGGGT AC | 27 |
| Fluorescent Primer 2 | SEQ ID NO.: 25 | HEX-CCGGGGATCCTCCTCAGTCGACCTG CA | 27 |
| endoV us | SEQ ID NO.: 26 | GAGATATACATATGGATCTCGCG | 23 |
| endoV int ds | SEQ ID NO.: 27 | GAATCGCCGGCATGGTGGTGGCGATGCG | 28 |
| endoV int us | SEQ ID NO.: 28 | ACCATGCCGGCGATTCCAGGTTTTCTTT CCTTC | 33 |
| endoV ds | SEQ ID NO.: 29 | TGGTGCTCGAGGGGCTGATTTGATG | 25 |
| DNA-G-Long-3' | SEQ ID NO.: 30 | GATATTCATCAATCGGAGTACGTTTTC | 27 |
| DNA-G-5' | SEQ ID NO.: 31 | ACAATCAACAACAAGCACGAATTCGAG | 27 |
| 7290R | SEQ ID NO.: 32 | AGTTCTTCTTTCGTCCCCIT | 20 |

TABLE 4-continued

| | Ref No. | Sequence (N-term-C-term; 5'→3') | Length |
|---|---|---|---|
| 7270R | SEQ ID NO.: 33 | CAGGCTGACATCACIIT | 17 |
| 7253R | SEQ ID NO.: 34 | TCAGTTGTTCACCCAGCIA | 19 |
| 7234R | SEQ ID NO.: 35 | GCGGAGACGGGCAATCAIT | 19 |
| 7215R | SEQ ID NO.: 36 | TCATCTTTCGTCATIIA | 17 |
| 7194R | SEQ ID NO.: 37 | TCCACAGAGAAACAATIIC | 19 |
| 7062F | SEQ ID NO.: 38 | ACCACCGGCGATCCIIC | 17 |
| 7079F | SEQ ID NO.: 39 | GCGTGAGTTCACCATIA | 17 |
| 7096F | SEQ ID NO.: 40 | TTCAGTCAGCACCGCTIA | 18 |
| 7111F | SEQ ID NO.: 41 | TGATGCTGCTGGCTIA | 16 |
| 7127F | SEQ ID NO.: 42 | CCCTGATGAGTTCGTIT | 17 |
| 7144F | SEQ ID NO.: 43 | CCGTACAACTGGCIT | 15 |
| T7-7158F-misA: | SEQ ID NO.: 44 | ATGACTGGTGGACAGCAAATGGGTAAAT TAATACGACTCACTATAGGGTT | 50 |
| Quencher-oligo | SEQ ID NO.: 45 | CCCTATAGTGAGTCGTATTAATTT-3iaBrqsP | 24 |
| Dye-oligo | SEQ ID NO.: 46 | ACCCAT/i6-TAMN/TTGCTGTCCACCA GTTAC | |
| F. primer 40FGI | SEQ ID NO.: 47 | GTTTTCCCAGTCACGACGTTGTAAAACG ACGICC | 34 |
| R. primer 40RGI | SEQ ID NO.: 48 | TCAAAGAAGTATTGCTACAACGG | 23 |
| F. primer: 40FGG | SEQ ID NO.: 49 | GTTTTCCCAGTCACGACGTTGTAAAACG ACGGCC | 34 |
| R. primer 40RGG | SEQ ID NO.: 50 | TCAAAGAAGTATTGCTACAACGG | 23 |
| Tban-1 forward primer: | SEQ ID NO.: 51 | GCAGATGAAGAAAAGGTTCTTGAGATTA TTCIT | 33 |
| Dye-P-3 | SEQ ID NO.: 52 | 5'-TAMRA Dye-AAATTAATACGACTC ACTATAGGGTTGAAGAATTAACAGAAGT AAAAGAGddC-3' | 51 |

Example 1

Preparation of the *B. cereus* Target DNA ("DNAG5")

*Bacillus cereus* strain 15816 from American Type Culture Collection (ATCC, Manassas, Va.) was grown according to the supplier's recommendations. A lyophilized culture of *B. cereus* was resuspended in 400 μL of Nutrient Broth then transferred to 5.6 ml of Nutrient Broth and incubated overnight at 30° C. with shaking. The Genomic DNA (gDNA) was isolated from the overnight liquid culture using MasterPure™ Gram Positive DNA Purification Kit (Epicentre® Biotechnologies, #GP1-60303) according to the manufacturer's instructions.

1. 4×1.0 ml of o/n culture was pelleted by centrifugation in separate 1.5 ml tubes.
2. Each pellet was resuspended in 100 μL TE Buffer by vortexing vigorously and added to separate 0.65 ml tubes.
3. The 1.5 ml tubes were rinsed with 50 μL each TE Buffer and the wash was combined with the appropriate 100 μL of resuspended pellet.
4. 1 μL of Ready-Lyse Lysozyme was added to each resuspended pellet, mixed, and incubated at 37° C. for 60 minutes.
5. 150 μL Gram Positive Lysis Solution & 1 μL Proteinase K Added to each tube and mixed.
6. Samples were incubated at 70° C. for 15 minutes vortexing every 5 minutes.
7. The samples were then cooled to 37° C. for 5 minutes and then placed on ice for 5 minutes.
8. 175 μL MPC Protein Precipitation Reagent was added to each tube.
9. The debris was pelleted at high speed in a microfuge for 10 minutes.
10. Supernatant was transferred to a clean 1.5 ml tube and the pellet was discarded.
11. 1 μL RNase A (5 μg/μl) was added to each tube and incubated 30 minutes at 37° C.

12. 500 μL 2-propanol was added to each tube and inverted 35 times to mix.
13. The tubes were centrifuged 10 minutes at high speed in a microfuge to pellet the DNA.
14. Each pellet was rinsed with 70% ethanol, dried, and resuspended in 35 μL TE buffer.
15. 1 μL from each prep was run on a 1% agarose gel.

Approximately 100 ng of B. cereus gDNA was amplified in four separate reactions using PuReTaq Ready-To-Go PCR Beads (GE Healthcare) and 5 μM of each primer, DNA-G-Long-3' (SEQ ID NO.:30) and DNA-G-5' (SEQ ID NO.:31). Thermal cycling conditions were:
1. 95° C. for 5 minutes
2. 95° C. for 30 seconds
3. 50° C. for 30 seconds
4. 72° C. for 1 minute
5. Steps 2-4 were repeated 31 times,
6. Held at +4° C.

One-tenth of each completed reaction was analyzed by electrophoresis using a 1% agarose gel. A 2181 base pair product was generated and used as the target DNA. Following analysis, the four amplification reactions were pooled and diluted in TE Buffer±0.01% Tween 20 prior to use.

Example 2

Single Primer, 2 Primers, Various Polymerases

Figure 4:
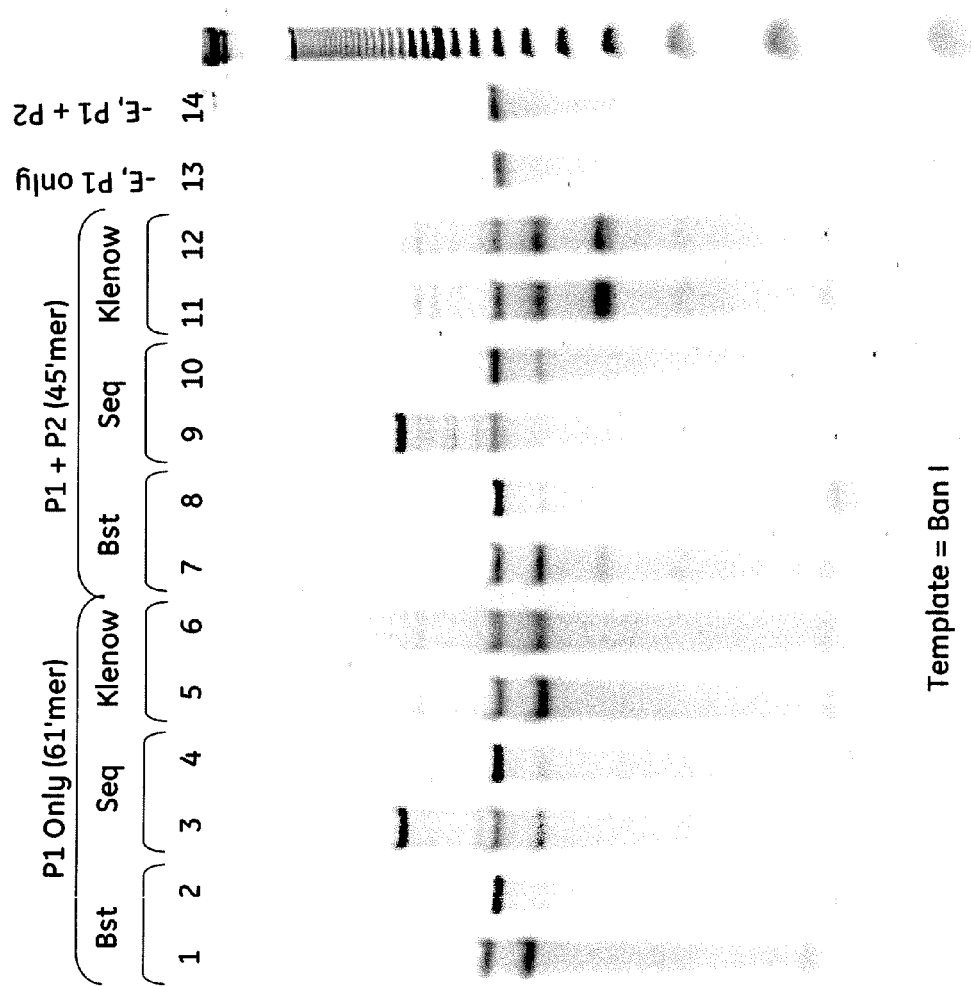
FIG. 4 depicts the use of a variety of polymerases to produce amplicons from a target DNA ("Ban 1"), in which a single primer or multiple primers (forward and reverse) were employed as described in the Example 2.

T7 DNA polymerase (Sequenase) and Klenow fragment were compared according to the reaction scheme presented below in Table 5, in which volumes indicated are microliters. P1 corresponds to SEQ ID NO.: 5 and P2-1 corresponds to SEQ ID NO.:6. Reactions 1, 2, 7, and 8 were incubated at 43° C. for 3 hours. The remaining reactions were incubated at 37° C. for 3 hours. Following storage at −20° C., the reactions were run on a 15% acrylamide (Invitrogen), 7M-urea gel. The results are shown in FIG. 4.

TABLE 5

| Reagent | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 10X Endonuclease V Buffer | 1 | | 1 | | 1 | | 1 | | 1 | | 1 | | 1 | 1 |
| 10X TP Buffer | | 1 | | | | | | 1 | | | | | 0.5 | 0.5 |
| 10X T7 Buffer | | | | 1 | | | | | | 1 | | | 0.5 | 0.5 |
| 10X Klenow Buffer | | | | | | 1 | | | | | | 1 | | 0.5 |
| Ban 1 Template | 0.5 | 0.5 | 0.5 | 0.5 | 0.5 | 0.5 | 0.5 | 0.5 | 0.5 | 0.5 | 0.5 | 0.5 | 0.5 | 0.5 |
| P1 | 0.5 | 0.5 | 0.5 | 0.5 | 0.5 | 0.5 | 0.5 | 0.5 | 0.5 | 0.5 | 0.5 | 0.5 | 2 | 2 |
| P2 | | | | | | | 0.5 | 0.5 | 0.5 | 0.5 | 0.5 | 0.5 | | |
| T4 g32p | 0.5 | 0.5 | 0.5 | 0.5 | 0.5 | 0.5 | 0.5 | 0.5 | 0.5 | 0.5 | 0.5 | 0.5 | | |
| Ethylene Glycol | 2 | 2 | 2 | 2 | 2 | 2 | 2 | 2 | 2 | 2 | 2 | 2 | | |
| Bst | 0.5 | 0.5 | | | | | 0.5 | 0.5 | | | | | 0.5 | 0.5 |
| T7 | | | 0.5 | 0.5 | | | | | 0.5 | 0.5 | | | 5 | 5 |
| Klenow | | | | | 0.5 | 0.5 | | | | | 0.5 | 0.5 | 10 | 10 |
| Endonuclease V | 0.5 | 0.5 | 0.5 | 0.5 | 0.5 | 0.5 | 0.5 | 0.5 | 0.5 | 0.5 | 0.5 | 0.5 | | |
| Water | 4.5 | 4.5 | 4.5 | 4.5 | 4.5 | 4.5 | 4 | 4 | 4 | 4 | 4 | 4 | | |
| Total Volume | 10 | 10 | 10 | 10 | 10 | 10 | 10 | 10 | 10 | 10 | 10 | 10 | | |

Example 3

Multiple Sets Of Primers And Single Strand Binding Protein 4, 6, and 12 mixes of primers were combined as shown below in Tables 6-13. The primer mixes were prepared so that one addition would add 10 pmol [final concentration] of each oligo to the reaction mixture.

12 Mix

TABLE 6

| Oligo |
|---|
| P-1 |
| P2-1 |
| 1275 |
| 1294 |
| 1313 |
| 1333 |
| 1378 |
| 1482 |
| 1517 |
| 1534 |
| 1560 |
| 1579 |

6 Mix

TABLE 7

| Oligo |
|---|
| P-1 |
| P2-1 |
| 1333 |
| 1378 |
| 1482 |
| 1517 |

4 Mix (4185-14 'E')

TABLE 8

| Oligo |
|---|
| P-1 |
| P2-1 |
| 1378 |

TABLE 8-continued

| Oligo |
|---|
| 1482 |

Internal 4 Mix

TABLE 9

| Oligo |
| --- |
| 1354 (645 pmol/uL) |
| 1333 (681 pmol/uL) |
| 1498 (732 pmol/uL) |
| 1517 (671 pmol/uL) |

Reaction Scheme: DNAG5 was diluted 1:100 in TE buffer. 10×HEMT buffer includes 100 mM HEPES (pH 8), 1 mM EDTA, 0.1% Tween 20, and 30 mM $MgCl_2$.

TABLE 10

| Component | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| DNAG5 1:100 | − | − | − | − | − | − | − | + | + | + | + | + |
| 12 mix | + | − | − | − | − | − | − | + | − | − | − | − |
| 6 mix | − | + | − | − | − | − | − | − | + | − | − | − |
| 4 mix | − | − | + | − | + | + | − | − | − | + | − | − |
| Internal 4 Mix | − | − | − | + | − | − | + | − | − | − | + | + |
| SSB, 1 µg/uL | + | − | − | + | − | + | + | − | − | − | + | − |
| SSB, 10 ng/uL | − | + | + | − | + | − | + | − | + | + | − | + |
| 1354 (10 pmol/uL) | − | − | − | − | − | − | − | − | − | − | − | − |
| 1333 (10 pmol/uL) | − | − | − | − | − | − | − | − | − | − | − | − |
| 1498 (10 pmol/uL) | − | − | − | − | − | − | − | − | − | − | − | − |
| 1517 (10 pmol/uL) | − | − | − | − | − | − | − | − | − | − | − | − |

| Component | 13 | 14 | 15 | 16 | 17 | 18 | 19 | 20 | 21 | 22 | 23 | 24 |
| --- | --- | --- | --- | --- | --- | --- | --- | --- | --- | --- | --- | --- |
| DNAG5 1:100 | + | + | + | + | + | + | − | − | − | − | − | − |
| B. cereus DNA (100 ng/uL) | − | − | − | − | − | − | + | + | + | + | + | + |
| 12 mix | − | − | − | − | − | + | − | − | − | − | − | − |
| 6 mix | + | + | − | − | − | − | + | − | − | − | − | − |
| 4 mix | − | − | + | + | + | + | − | − | + | − | + | + |
| Internal 4 Mix | − | − | − | + | + | − | − | − | − | + | + | + |
| SSB, 1 µg/uL | + | + | − | + | + | − | − | − | − | − | − | + |
| SSB, 10 ng/uL | − | − | + | + | + | + | + | + | + | + | + | − |
| 1354 (10 pmol/uL) | + | − | + | − | − | − | − | − | − | − | − | − |
| 1333 (10 pmol/uL) | + | − | − | + | − | − | − | − | − | − | − | − |
| 1498 (10 pmol/uL) | − | + | + | − | − | − | − | − | − | − | − | − |
| 1517 (10 pmol/uL) | − | + | − | − | − | − | − | − | − | − | − | − |

Bulk Denaturation Mixes (Volumes Shown in Tables are in Microliters Unless Otherwise Indicated.)

TABLE 11

| Component/ID | A (X5) | B (X5) | C (X15) | D (X13) |
| --- | --- | --- | --- | --- |
| 10X HEMT Buffer | 5 | 5 | 15 | 13 |
| 12 mix | 2.5 | — | — | — |
| 6 mix | — | 2.5 | — | — |
| 4 mix | — | — | 7.5 | — |
| Internal 4 Mix | — | — | — | 6.5 |
| Water | 10 | 10 | 7.5 | 7.5 |
| Total Volume | 17.5 | 17.5 | 30 | 26 |

3.5 µL of 'A' were added to each of 1, 8, and 19; 3.5 µL of 'B' were added to each of 2, 9, and 20; 2.0 µL of 'C' were added to each of 3, 6, 7, 10, 13, 14, 15, 16, 17, 18, 21, 23, and 24; and 2.0 µL of 'D' were added to each of 4, 5, 6, 7, 11, 12, 17, 18, 22, 23, and 24.

Denaturations

TABLE 12

| Component | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| DNAG5 1:100 | — | — | — | — | — | — | — | 1 | 1 | 1 | 1 | 1 |
| Bulk Denaturation Mix A | 3.5 | — | — | — | — | — | — | 3.5 | — | — | — | — |
| Bulk Denaturation Mix B | — | 3.5 | — | — | — | — | — | — | 3.5 | — | — | — |
| Bulk Denaturation Mix C | — | — | 2 | — | — | 2 | 2 | — | — | 2 | — | — |
| Bulk Denaturation Mix D | — | — | — | 2 | 2 | 2 | 2 | — | — | — | 2 | 2 |
| 1354 (10 pmol/uL) | — | — | — | — | — | — | — | — | — | — | — | — |
| 1333 (10 pmol/uL) | — | — | — | — | — | — | — | — | — | — | — | — |
| 1498 (10 pmol/uL) | — | — | — | — | — | — | — | — | — | — | — | — |
| 1517 (10 pmol/uL) | — | — | — | — | — | — | — | — | — | — | — | — |
| Water | 1.5 | 1.5 | 3 | 3 | 3 | 1 | 1 | 0.5 | 0.5 | 2 | 2 | 2 |
| Total Vol. | 5 | 5 | 5 | 5 | 5 | 5 | 5 | 5 | 5 | 5 | 5 | 5 |

| Component | 13 | 14 | 15 | 16 | 17 | 18 | 19 | 20 | 21 | 22 | 23 | 24 |
| --- | --- | --- | --- | --- | --- | --- | --- | --- | --- | --- | --- | --- |
| DNAG5 1:100 | 1 | 1 | 1 | 1 | 1 | 1 | — | — | — | — | — | — |
| B. cereus gDNA (100 ng/uL) | — | — | — | — | — | — | 1 | 1 | 1 | 1 | 1 | 1 |
| Bulk Denaturation Mix A | — | — | — | — | — | — | 3.5 | — | — | — | — | — |
| Bulk Denaturation Mix B | 2 | 2 | — | — | — | — | — | 3.5 | — | — | — | — |
| Bulk Denaturation Mix C | — | — | 2 | 2 | 2 | 2 | — | — | 2 | — | 2 | 2 |
| Bulk Denaturation Mix D | — | 1 | — | — | 2 | 2 | — | — | — | 2 | 2 | 2 |
| 1354 (10 pmol/uL) | 1 | — | 1 | — | — | — | — | — | — | — | — | — |
| 1333 (10 pmol/uL) | 1 | — | — | 1 | — | — | — | — | — | — | — | — |
| 1498 (10 pmol/uL) | — | 1 | 1 | — | — | — | — | — | — | — | — | — |

TABLE 12-continued

| | | | | | | | | | | | | |
|---|---|---|---|---|---|---|---|---|---|---|---|---|
| 1517 (10 pmol/uL) | — | — | — | 1 | — | — | — | — | — | — | — | — |
| Water | 5 | 5 | — | — | — | — | 0.5 | 0.5 | 2 | 2 | — | — |
| Total Vol. | 5 | 5 | 5 | 5 | 5 | 5 | 5 | 5 | 5 | 5 | 5 | 5 |

Bulk Enzyme Mixes: 10 Rxn Buffer Used in Table 13: 100 mM HEPES, 30 mM $MgCl_2$, 0.1% Tween 20, 2.5 mM each dNTP, and 10 mM TCEP.

TABLE 13

| Component/ID | 1X | X (X10) | Z (X18) |
|---|---|---|---|
| 10X Reaction Buffer) | 1 | 10 | 18 |
| 100% Ethylene Glycol | 1 | 10 | 18 |
| E coli SSB, 1 µg/uL | 1 | 10 | — |
| E coli SSB, 10 ng/uL | — | — | 18 |
| ΔTts (20 U/) | 1 | 10 | 18 |
| Endonuclease V (40 pmol/) | 0.075 | 0.75 | 1.35 |
| Water | 0.925 | 9.25 | 16.65 |
| Total Volume | 5 | 50 | 90 |

5 µL of "X" were added to each of reaction mixes 1, 4, 6, 8, 11, 17, 18, and 24; 5 µL of "Z" were added to each of 2, 3, 5, 7, 9, 10, 12, 13, 15, 16, 19, 20, 21, 22, and 23. All reaction mixtures were incubated at 45° C. for 75 minutes and an $\frac{1}{10}^{th}$ aliquot was analyzed on a 10% TB Urea gel, in which each of the oligo mixtures generated product of the expected sizes.

Example 4

Isothermal Amplification Using Internal 6 Oligo Mix

Selected oligos were removed from the 6-oligo mix to determine which oligo or oligos caused the doublet band between 70 and 80 bases. Also, variations divalent cation and single strand binding protein concentrations were tested.

Oligo Mixes

TABLE 14

| Oligo | A OM | B OM |
|---|---|---|
| P-1 (972 pmol/uL) | 1.03 µL | — |
| P2-1 (335 pmol/uL) | 2.99 µL | 2.99 µL |
| 1333 (681 pmol/uL) | 1.47 µL | 1.47 µL |
| 1378 (645 pmol/uL) | 1.55 µL | 1.55 µL |
| 1482 (661 pmol/uL) | — | 1.51 µL |
| 1517 (671 pmol/uL) | 1.49 µL | 1.49 µL |
| TE + 0.01% Tween 20 | 41.47 µL | 40.99 µL |
| Total Volume | 50 µL | 50 µL |

Reaction Scheme 10 Rxn Buffer A used in Table 15: 100 mM HEPES, 30 mM $MgCl_2$, 0.1% Tween 20, 2.5 mM each dNTP, and 10 mM TCEP. 10 Rxn Buffer B used in Table 15: 100 mM HEPES, 60 mM $MgCl_2$, 0.1% Tween 20, 2.5 mM each dNTP, and 10 mM TCEP.

TABLE 15

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | − | − | − | + | + | + | + | − | − | − | − | + | + |
| DNAG5 1:100 | − | − | − | − | − | − | − | − | + | + | + | + | − | − |
| 12 Mix | + | − | − | − | + | − | − | − | + | + | − | − | + | + |
| 6 Mix | − | + | − | − | − | + | − | − | − | + | + | − | − | − |
| A OM | − | − | + | − | − | − | + | − | − | − | − | − | − | − |
| B OM | − | − | − | + | − | − | − | + | − | − | − | − | − | − |
| Rxn Buffer A (3 mM) | − | − | − | − | − | − | − | − | − | − | + | + | − | − |
| Rxn Buffer B (6 mM) | + | + | + | + | + | + | + | + | + | + | − | − | + | + |
| 30 mM Mg | − | − | − | − | − | − | − | − | − | − | − | − | + | − |
| 60 mM Mg | − | − | − | − | − | − | − | − | − | − | − | − | − | + |
| 90 mM Mg | − | − | − | − | − | − | − | − | − | − | − | − | − | − |
| SSB, 1 ng/rxn | − | − | − | − | − | − | − | − | + | − | + | − | − | − |
| SSB, 1 µg/rxn | + | + | + | + | + | + | + | + | − | + | − | + | + | + |

| Component | ID | | | | | | | | | | | | | |
|---|---|---|---|---|---|---|---|---|---|---|---|---|---|---|
| | 15 | 16 | 17 | 18 | 19 | 20 | 21 | 22 | 23* | 24* | 25* | 26* | 27* | 28* |
| DNAG5 1:10 | + | + | + | + | − | − | − | − | − | − | − | − | − | − |
| DNAG5 1:100 | − | − | − | − | − | − | − | − | − | − | − | − | − | − |
| B. cereus gDNA 100 ng/rxn | + | − | − | − | + | + | + | + | − | − | − | − | − | − |
| 12 Mix | − | − | − | − | + | − | − | − | + | + | + | − | − | − |

TABLE 15-continued

| | | | | | | | | | | | | | | |
|---|---|---|---|---|---|---|---|---|---|---|---|---|---|---|
| 6 Mix | − | + | + | + | − | + | − | − | − | − | − | + | + | + |
| A OM | − | − | − | − | − | − | + | − | − | − | − | − | − | − |
| B OM | − | − | − | − | − | − | − | + | − | − | − | − | − | − |
| Rxn Buffer A (3 mM) | + | − | − | − | − | − | − | − | − | − | − | − | − | − |
| Rxn Buffer B (6 mM) | − | + | + | + | + | + | + | + | + | + | + | + | + | + |
| 30 mM Mg | − | + | − | − | − | − | − | − | + | − | − | + | − | − |
| 60 mM Mg | + | − | + | − | − | − | − | − | − | + | − | − | + | − |
| 90 mM Mg | − | − | − | + | − | − | − | − | − | − | + | − | − | + |
| SSB, 1 ng/rxn | + | − | − | − | − | − | − | − | − | − | − | − | − | − |
| SSB, 1 µg/uL | | + | + | + | + | + | + | + | + | + | + | + | + | + |

*Extra MgCl₂ added to denaturation

No Template Control Denaturations 10×HE Buffer: 100 mM HEPES (pH*), 1 mM EDTA.

TABLE 16

| | ID | | | | |
|---|---|---|---|---|---|
| Component | 1 | 2 | 3 | 4 | 23 |
| 10X HE Buffer | 1 µL | 1 µL | 1 µL | 1 µL | 1 µL |
| DNAG5 1:10 | — | — | — | — | — |
| DNAG5 1:100 | — | — | — | — | — |
| 12 Mix | 0.5 µL | — | — | — | 0.5 µL |
| 6 Mix | — | 0.5 µL | — | — | — |
| A OM | — | — | 0.5 µL | — | — |
| B OM | — | — | — | 0.5 µL | — |
| 30 mM MgCl₂ | — | — | — | — | 1 µL |
| 60 mM MgCl₂ | — | — | — | — | — |
| 90 mM MgCl₂ | — | — | — | — | — |
| Water | 2.5 µL | 2.5 µL | 2.5 µL | 2.5 µL | 1.5 µL |
| Total Volume | 4 µL | 4 µL | 4 µL | 4 µL | 4 µL |

| | ID | | | | |
|---|---|---|---|---|---|
| Component | 24 | 25 | 26 | 27 | 28 |
| 10X HE Buffer | 1 µL | 1 µL | 1 µL | 1 µL | 1 µL |
| DNAG5 1:10 | — | — | — | — | — |
| DNAG5 1:100 | — | — | — | — | — |
| 12 Mix | 0.5 µL | 0.5 µL | — | — | — |
| 6 Mix | — | — | 0.5 µL | 0.5 µL | 0.5 µL |
| A OM | — | — | — | — | — |
| B OM | — | — | — | — | — |
| 30 mM MgCl₂ | — | — | — | 1 µL | — |
| 60 mM MgCl₂ | 1 µL | — | — | — | 1 µL |

Bulk Denaturation Mixes

TABLE 17

| | ID | | | |
|---|---|---|---|---|
| Component | A (X6) | B (X6) | C (X3) | D (X3) |
| 10X HE Buffer | 6 µL | 6 µL | 3 µL | 3 µL |
| DNAG5 1:10 | 6 µL | 6 µL | — | — |
| DNAG5 1:100 | — | — | 3 µL | 3 µL |
| 12 Mix | 3 µL | — | 1.5 µL | — |
| 3 Mix | — | 3 µL | — | 1.5 µL |
| OM A | — | — | — | — |
| OM B | — | — | — | — |
| Water | 9 µL | 9 µL | 4.5 µL | 4.5 µL |
| Total Volume | 24 µL | 24 µL | 12 µL | 12 µL |

4 µL "A" in each of 5, 13, 14, and 15
4 µL "B" in each of 6, 16, 17, and 18
4 µL "C" in each of 9 and 10
4 µL "D" in each of 11 and 12
Denaturations

TABLE 18

| | ID | | | | | |
|---|---|---|---|---|---|---|
| Component | 7 | 8 | 19 | 20 | 21 | 22 |
| 10X HE Buffer | 1 µL | 1 µL | 1 µL | 1 µL | 1 µL | 1 µL |
| DNAG5 1:10 | 1 µL | 1 µL | — | — | — | — |
| DNAG5 1:100 | — | — | — | — | — | — |
| *B. cereus* gDNA 100 ng/uL | — | — | 1 µL | 1 µL | 1 µL | 1 µL |
| 12 Mix | — | — | 0.5 µL | — | — | — |
| 3 Mix | — | — | — | 0.5 µL | — | — |
| OM A | 0.5 µL | — | — | — | 0.5 µL | — |
| OM B | — | 0.5 µL | — | — | — | 0.5 µL |
| 30 mM MgCl₂ | — | — | — | — | — | — |
| 60 mM MgCl₂ | — | — | — | — | — | — |
| 90 mM MgCl₂ | — | — | — | — | — | — |
| Water | 1.5 µL | 1.5 µL | 1.5 µL | 1.5 µL | 1.5 µL | 1.5 µL |
| Total Volume | 4 µL | 4 µL | 4 µL | 4 µL | 4 µL | 4 µL |

Bulk Enzyme Mixes

TABLE 19

| Component | V (X2) | W (X2) | X (X2) | Y (X8) | Z (X21) |
|---|---|---|---|---|---|
| 10X Rxn Buffer A (3 mM) | 2 μL | 2 μL | — | — | — |
| 10X Rxn Buffer B (6 mM) | — | — | 2 μL | 8 μL | 21 μL |
| 100% Ethylene Glycol | 2 μL | 2 μL | 2 μL | 8 μL | 21 μL |
| E. coli SSB (1 ng/uL) | 2 μL | — | 2 μL | — | — |
| E. coli SSB (1 μg/uL) | — | 2 μL | — | 8 μL | 21 μL |
| ΔTts (20 U/uL) | 2 μL | 2 μL | 2 μL | 8 μL | 21 μL |
| Endo V (40 pmol/uL) | 0.15 μL | 0.15 μL | 0.15 μL | 0.6 μL | 1.58 μL |
| Water | 3.85 μL | 3.85 μL | 3.85 μL | 7.4 μL | 85.58 μL |
| Total Volume | 12 μL | 12 μL | 12 μL | 40 μL | 126 μL |

6 μL "V" in 11
6 μL "W" in 12
6 μL "X" in 9
5 μL "Y" in 13-18 (Add amt MgCl$_2$ in 1 μL volume)
6 μL "Z" in each of 1-8, 10, and 19-28

Figure 5:
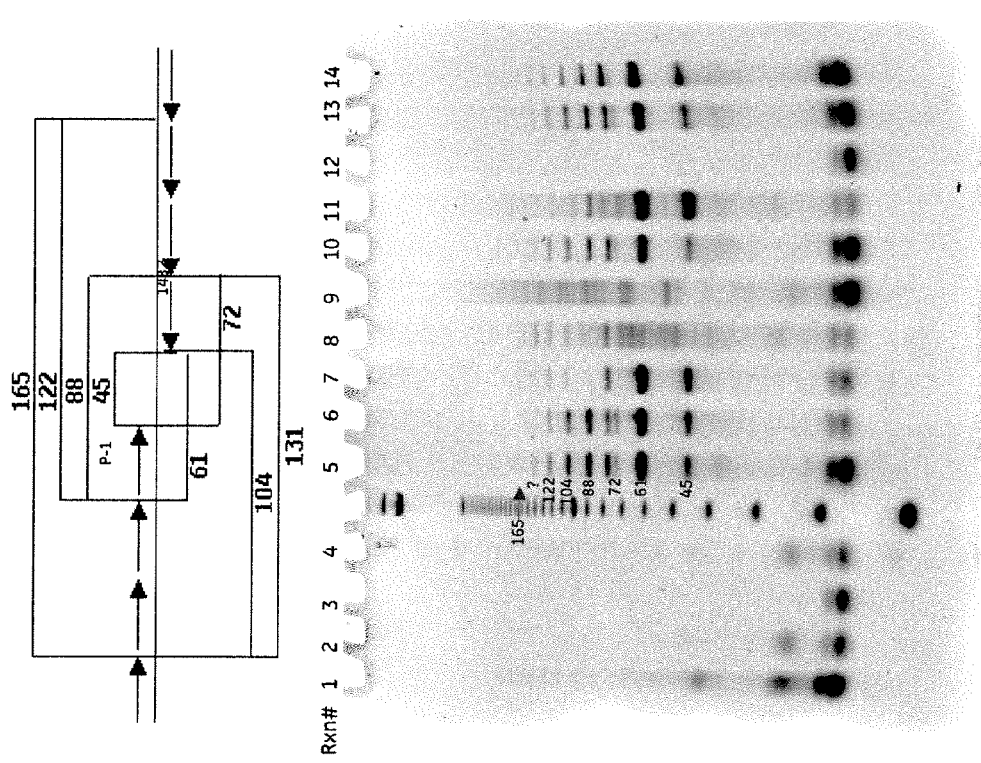
FIG. 5 depicts amplicon production using multiple sets of nested primers in several different reaction mixtures as described in Example 4.

All reactions were incubated at 45° C. for 75 minutes and applied to a gel as shown in FIG. 5.

Example 5

In Vitro Transcription (IVT)

Bulk Standard Isothermal Amplification Reaction. Template Primer Mix 0.08 pmol; SEQ ID NO.: 4; 2 pmol SEQ ID NO.: 5; 10 pmol SEQ ID NO.: 6; and 18 pmol SEQ ID NO.: 7.

TABLE 20

| Component | 1X | 3X |
|---|---|---|
| 10X Endonuclease V Buffer | 1 | 3 |
| Template Primer Mix | 0.5 | 1.5 |
| Klenow (10 U/μL) | 0.5 | 1.5 |
| Endonuclease V (8 pmol/μL) | 0.5 | 1.5 |
| ThermoFidelase | 1 | 3 |
| TAP/T4 g32p (0.005 U TAP; 0.2 μg T4g32P) | 0.5 | 1.5 |
| Water | 6 | 18 |
| Total Vol. | 10 | 30 |

3 μL of the 3× bulk reaction were added to 6 μL GLB (gel loading buffer) II (Before isothermal amplification). The remaining 3× bulk reaction was incubated at 45° C. for 75 minutes. The reaction was stopped by adding 2.7 μL, 110 mM EDTA. A 1-μL aliquot from the reaction was added to 2 GLB II (After isothermal amplification). Beta-Mercaptoethanol (β-ME) was obtained from Sigma (cat. #104K0161). 1M Tris-HCl, pH 8 was obtained from Ambion (cat. #105R055626A). The rNTP mixtures are shown in Table 21 below and the general reaction mixture for in vitro transcription is shown below in Table 22. For this example, components of MEGAscript T7 Kit (Ambion) were used.

TABLE 21

| Component | Amt |
|---|---|
| 75 mM ATP | 15 μL |
| 75 mM CTP | 15 μL |
| 75 mM GTP | 15 μL |
| 75 mM UTP | 15 μL |
| Total Volume | 60 μL |

TABLE 22

| Component | Amt |
|---|---|
| Water | 3 μL |
| rNTP Mix | 4 μL |
| 10X Buffer | 1 μL |
| Template | 1 μL |
| T7 Enzyme Mix | 1 μL |
| Total Volume | 10 μL |

(1.) 10×IVT Buffer—Tris/MgCl$_2$/DTT

TABLE 23

| Component | 1X |
|---|---|
| Water | 300 μL |
| 1M Tris-HCl, pH 8 | 400 μL |
| 1M DTT | 100 μL |
| 1M MgCl$_2$ | 200 μL |
| Total Volume | 1 ml |

TABLE 24

185 mM MgCl$_2$
10 1M MgCl$_2$
44 Water
Total Volume 54

TABLE 25

150 mM NaCl
3 5 M NaCl
97 μL Water
Total Volume 100 μL (2) 10×IVT Buffer—Tris/MgCl$_2$/β-mercaptoethanol

TABLE 26

| Component | 1X |
| --- | --- |
| Water | 299 μL |
| 1M Tris-HCl, Ph 8 | 400 μL |
| 99% β-ME | 101 μL |
| 1M MgCl$_2$ | 200 μL |
| Total Volume | 1 ml |

(3) 10×IVT Buffer—HEPES/MgCl$_2$/DTT

TABLE 27

| Component | 1X |
| --- | --- |
| Water | 300 μL |
| 1M HEPES, pH 8 | 400 μL |

TABLE 27-continued

| Component | 1X |
| --- | --- |
| 1M DTT | 100 μL |
| 1M MgCl$_2$ | 200 μL |
| Total Volume | 1 ml |

(4) 10×IVT Buffer—HEPES/MgCl$_2$/β-ME

TABLE 28

| Component | 1X |
| --- | --- |
| Water | 299 μL |
| 1M HEPES, pH 8 | 400 μL |
| 99% β-ME | 101 μL |
| 1M MgCl$_2$ | 200 μL |
| Total Volume | 1 ml |

Reaction Scheme All reactions used 1 μL of the Bulk Standard IA Reaction. MgCl$_2$ addition of 18.5 mM (20 mM [final]). NaCl addition of 15 mM ([final]). The reaction mixtures used are shown in Table 29.

TABLE 29

| Component | ID 1 | 2 | 3 | 4 | 5 | 6 | 7 |
| --- | --- | --- | --- | --- | --- | --- | --- |
| Water | 3 | 1 | 3 | 2 | 3 | 2 | 3 |
| rNTP Mix | 4 | 4 | 4 | 4 | 4 | 4 | 4 |
| 10X IVT Buffer (Ambion) | 1 | 1 | — | — | — | — | — |
| 10X Rxn Buffer A | — | — | 1 | 1 | — | — | — |
| 10X Rxn Buffer B | — | — | — | — | 1 | 1 | — |
| 185 mM MgCl$_2$ | — | — | — | 1 | — | 1 | — |
| Glycerol | — | 2 | — | — | — | — | — |
| #1 10X IVT Buffer - Tris/MgCl$_2$/DTT | — | — | — | — | — | — | 1 |
| #2 10X IVT Buffer - Tris/MgCl$_2$/β-ME | — | — | — | — | — | — | — |
| Template | 1 | 1 | 1 | 1 | 1 | 1 | 1 |
| T7 Enzyme Mix (Ambion) | 1 | 1 | 1 | 1 | 1 | 1 | 1 |
| Total Volume | 10 | 10 | 10 | 10 | 10 | 10 | 10 |

| Component | ID 8 | 9 | 10 | 11 | 12 | 13 | 14 |
| --- | --- | --- | --- | --- | --- | --- | --- |
| Water | 3 | 3 | 3 | 2 | 2 | 2 | 2 |
| rNTP Mix | 4 | 4 | 4 | 4 | 4 | 4 | 4 |
| 150 mM NaCl | — | — | — | 1 | 1 | 1 | 1 |
| #1 10X IVT Buffer - Tris/MgCl$_2$/DTT | — | — | — | 1 | — | — | — |
| #2 10X IVT Buffer - Tris/MgCl$_2$/β-ME | — | — | — | — | 1 | — | — |
| #3 10X IVT Buffer - HEPES/MgCl$_2$/DTT | — | 1 | — | — | — | 1 | — |
| #4 10X IVT Buffer - HEPES/MgCl$_2$/β-ME | — | — | 1 | — | — | — | 1 |
| Template | — | 1 | 1 | 1 | 1 | 1 | 1 |
| T7 Enzyme Mix | 1 | 1 | 1 | 1 | 1 | 1 | 1 |
| Total Volume | 1 | 10 | 10 | 10 | 10 | 10 | 10 |

Figure 6B:
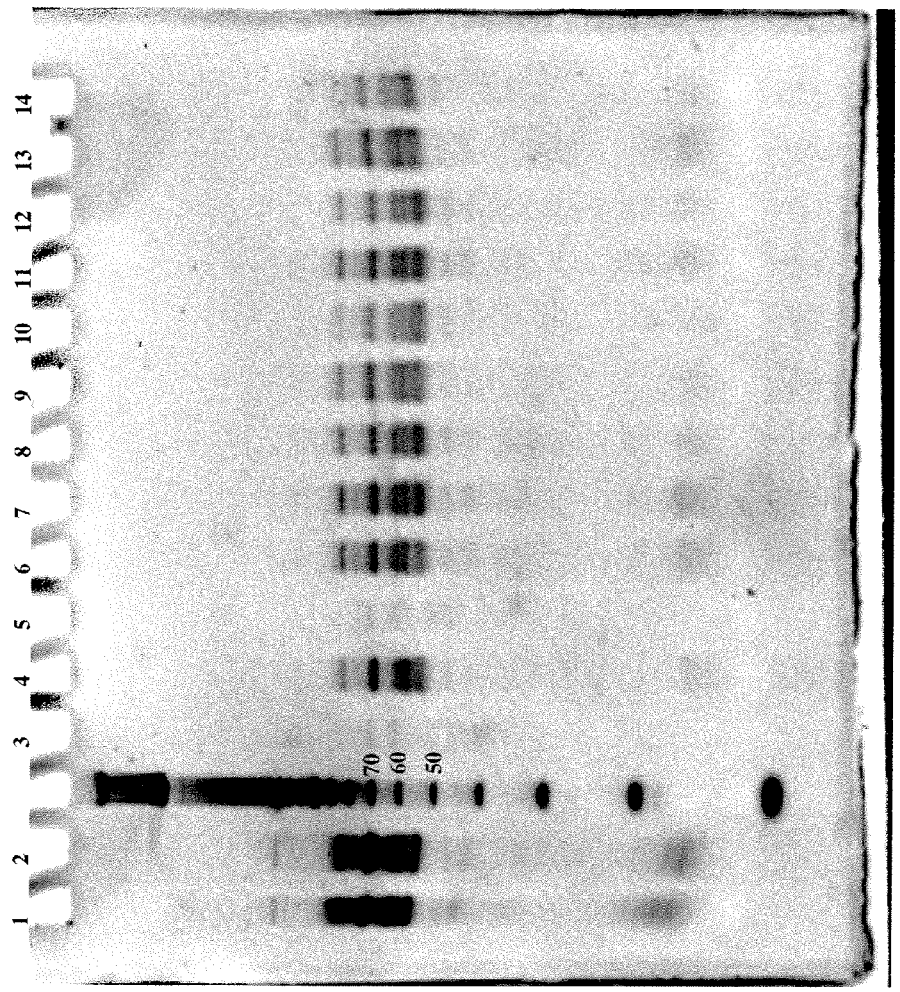
FIG. 6A shows a gel with the DNA products and FIG. 6B shows a gel with the RNA products.
Figure 6A:
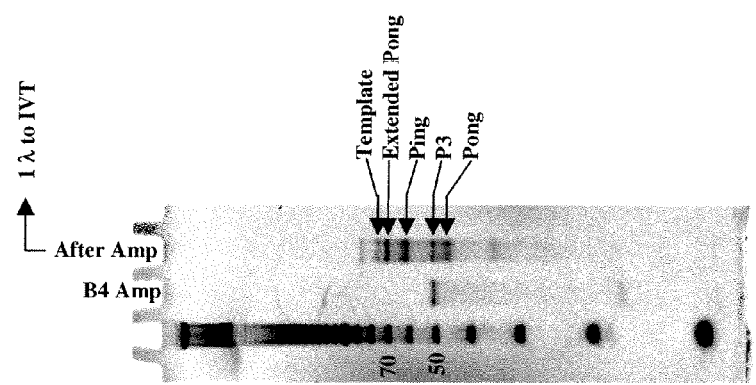

Each reaction, 1-14, was incubated at 37° C. for 2 hours and stopped by the addition of 20 µL GLB II. 3 µL reaction were loaded into a well of a 15% acrylamide 7M-urea TBE gel (Invitrogen), shown in FIG. 6B.

Example 6

Mixed Oligos; Mg Concentration; and SSB Concentration

The following experiment demonstrates that the addition of more than 1 ng of single strand binding protein to a 10-µL volume, increases fidelity and reduces background amplification significantly.

TABLE 30

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | − | − | − | − | − | − | − | + | + | + | + | + | + |
| DNAG5 1:100 | − | − | − | − | − | − | − | − | − | − | − | − | − | − |
| 3 mM MgCl2 | + | + | − | − | + | + | − | − | + | + | − | − | + | + |
| 6 mM MgCl2 | − | − | + | + | − | − | + | + | − | − | + | + | − | − |
| 12 Mix | + | + | + | + | − | − | − | − | + | + | + | + | − | − |
| 3 Mix | − | − | − | − | + | + | + | + | − | − | − | − | + | + |
| SSB 1 ng/reaction | + | − | + | − | + | − | + | − | + | − | + | − | + | − |
| SSB 1 µg/reaction | − | + | − | + | − | + | − | + | − | + | − | + | − | + |

| Component | ID | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| DNAG5 1:10 | + | + | − | − | − | − | − | − | − | − | + | + | + | + |
| DNAG5 1:100 | − | − | + | + | + | + | + | + | + | + | + | + | − | − |
| 3 mM MgCl2 | − | − | + | + | − | − | + | + | − | − | − | − | + | + |
| 6 mM MgCl2 | + | + | − | − | + | + | − | − | + | + | + | + | − | − |
| 12 Mix | − | − | + | + | + | + | − | − | − | − | − | − | + | + |
| 6 Mix | + | + | − | − | − | − | + | + | + | + | + | + | − | − |
| SSB 1 ng/reaction | + | − | + | − | + | − | + | − | + | − | − | + | − | + |
| SSB 1 µg/reaction | − | + | − | + | − | + | − | + | − | + | − | − | − | − |

Bulk Denaturation Mixes

TABLE 31

| Component | ID | | | | | |
|---|---|---|---|---|---|---|
| | A (X6) | B (X6) | C (X6) | D (X6) | E (X8) | F (X8) |
| 10X HE Buffer | 6 | 6 | 6 | 6 | 8 | 8 |
| DNAG5 1:10 | — | — | 6 | 6 | — | — |
| DNAG5 1:100 | — | — | — | — | 8 | 8 |
| 12 Mix | 3 | — | 3 | — | 4 | — |
| 3 Mix | — | 3 | — | 3 | — | 4 |
| Water | 15 | 15 | 9 | 9 | 12 | 12 |
| Total Volume | 24 | 24 | 24 | 24 | 32 | 32 |

4 µL "A" were added to each of reactions 1-4; 4 µL of "B" were added to each of reactions 5-8; 4 µL of "C" were added to each of reactions 9-12; 4 µL of "D" were added to each of reactions 13-16; 4 µL "E" were added to each of reactions 17-20, 25, 26; 4 µL "F" were added to each of reactions 21-24, 27, and 28.

Bulk Enzyme Mixes

TABLE 32

| Component | ID | | | |
|---|---|---|---|---|
| | W (X9) | X (X9) | Y (X9) | Z (X9) |
| 10X Reaction Buffer, 3 mM Mg$^{+2}$ | 9 | 9 | — | — |
| 10X Reaction Buffer, 6 mM Mg$^{+2}$ | — | — | 9 | 9 |
| 100% Ethylene Glycol | 9 | 9 | 9 | 9 |
| E coli SSB, 1 ng/µL | 9 | — | 9 | — |
| E coli SSB, 1 µg/µL | — | 9 | — | 9 |
| ATts (20 U/µl) | 9 | 9 | 9 | 9 |
| Endonuclease V (40 pmol/µL) | 0.63 | 0.63 | 0.63 | 0.63 |
| Water | 17.37 | 17.37 | 17.37 | 17.37 |
| Total Vol. | 54 | 54 | 54 | 54 |

6 µL of "W" were added to each of reactions 1, 5, 9, 13, 17, 21, and 25; 6 µL of "X" were added to each of reactions 2, 6, 10, 14, 18, 22, and 26; 6 µL of "Y" were added to each of reactions 3, 7, 11, 15, 19, 23, 27; and 6 µL of "Z" were added to each of reactions 4, 8, 12, 16, 20, 24, and 28.

Figure 7:
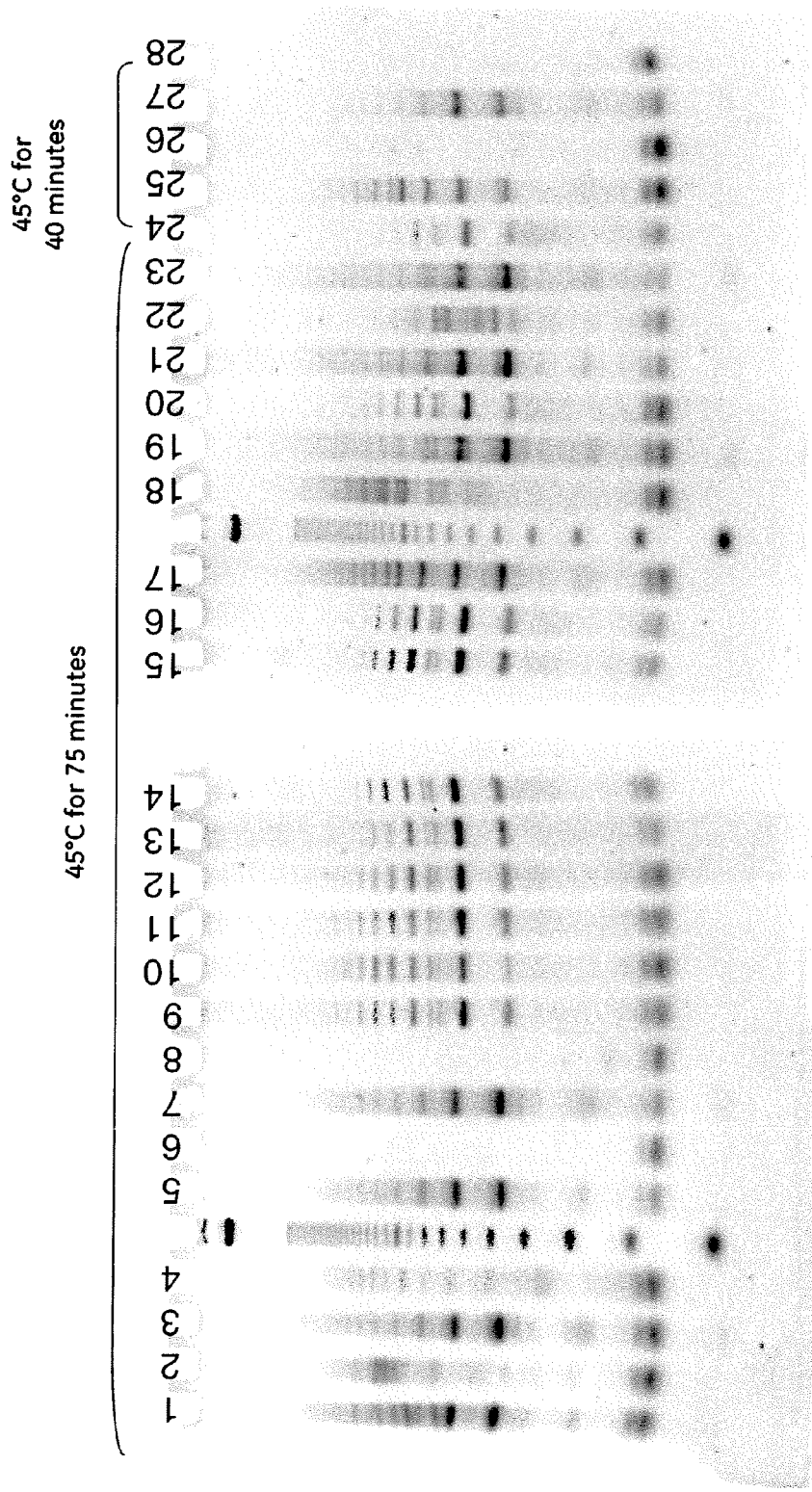
FIG. 7 shows the reaction products using a variety of SSB concentrations as described in Example 6.

Reactions 1-24 were incubated at 45° C. for 75 minutes and reactions 25-28 were incubated 45° C. for 40 minutes. A $\frac{1}{10}^{th}$ aliquot of each reaction was analyzed on a 10% TB Urea gel (Invitrogen), which is shown in FIG. 7.

Example 7

Extender Templates; dd terminators and Mismatched Primers

TABLE 33

12 Mix
Dye-P-3, 4133-92
cP-3 3' Quencher SEQ ID NO.: 23
P-3 Mismatched SEQ ID NO.: 8
P-3SD Mod (ddC) SEQ ID NO.: 10
P-3 NO ddC SEQ ID NO.: 9
All oligos were diluted in TE + 0.01% Tween 20 to 10 pmol/uL

Reaction Scheme

TABLE 34

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | + | + | − | − | − | − | + | + | + | + | + | + | + |
| DNAG5 1:100 | − | − | − | + | + | − | − | − | − | − | − | − | − | − |
| DNAG5 1:1000 | − | − | − | − | − | + | + | − | − | − | − | − | − | − |
| 12 Mix | + | + | + | + | + | + | + | + | + | + | + | + | − | − |
| 12 Mix less SEQ ID NO.: 17 | − | − | − | − | − | − | − | − | − | − | − | − | + | + |
| P-3 SD Mod | − | − | − | − | − | − | − | + | − | − | − | − | − | − |
| P-3 NO ddC | − | − | − | − | − | − | − | − | + | − | − | − | − | − |
| P-3 Mismatched | − | − | − | − | − | − | − | − | − | + | − | − | − | − |
| cP-3 3' Quencher | − | − | − | − | − | − | − | − | − | − | + | − | − | − |
| Dye-P-3 | − | − | − | − | − | − | − | − | − | − | − | + | − | − |
| ROX-11-ddG (3 pmol/) | − | − | + | − | + | − | + | − | − | − | − | − | − | + |

Bulk Enzyme Mix

TABLE 36

| Component | 1X | A (X12) | B (X6) |
|---|---|---|---|
| 10X Reaction Buffer | 1 | 12 | 6 |
| 100% Ethylene Glycol | 1 | 12 | 6 |
| SYBR Green I (1:2000) | 1 | 12 | 6 |
| ROX-11-ddGTP | 1 | — | 6 |
| ΔTts (20 U/uL) | 1 | 12 | 6 |
| Endonuclease V | 0.075 | 0.9 | 0.45 |
| SSB (1 ng/uL) | 1 | 12 | 6 |
| Water | — | 12 | — |
| Total Vol. (uL) | 6.075 | 72.9 | 36.45 |

Denaturations

TABLE 35

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 10X HE Buffer | 1 | 1 | 1 | 1 | 1 | 1 | 1 | 1 | 1 | 1 | 1 | 1 | 1 | 1 |
| DNAG1:10 | — | 1 | 1 | — | — | — | — | 1 | 1 | 1 | 1 | 1 | 1 | 1 |
| DNAG1:100 | — | — | — | 1 | 1 | — | — | — | — | — | — | — | — | — |
| DNAG1:1000 | — | — | — | — | — | 1 | 1 | — | — | — | — | — | — | — |
| 12 Mix | 0.5 | 0.5 | 0.5 | 0.5 | 0.5 | 0.5 | 0.5 | 0.5 | 0.5 | 0.5 | 0.5 | 0.5 | — | — |
| 12 Mix Less SEQ ID NO.: 17 | — | — | — | — | — | — | — | — | — | — | — | — | 0.5 | 0.5 |
| P-3SD Mod | — | — | — | — | — | — | — | 1 | — | — | — | — | — | — |
| P-3N OddC | — | — | — | — | — | — | — | — | 1 | — | — | — | — | — |
| P-3 Mismatched | — | — | — | — | — | — | — | — | — | 1 | — | — | — | — |
| cP-33' Quencher | — | — | — | — | — | — | — | — | — | — | 1 | — | — | — |
| Dye-P-3 | — | — | — | — | — | — | — | — | — | — | — | 1 | — | — |
| Water | 2.5 | 1.5 | 1.5 | 1.5 | 1.5 | 1.5 | 1.5 | 0.5 | 0.5 | 0.5 | 0.5 | 0.5 | 1.5 | 1.5 |
| Total Volume | 4 | 4 | 4 | 4 | 4 | 4 | 4 | 4 | 4 | 4 | 4 | 4 | 4 | 4 |

Figure 8:
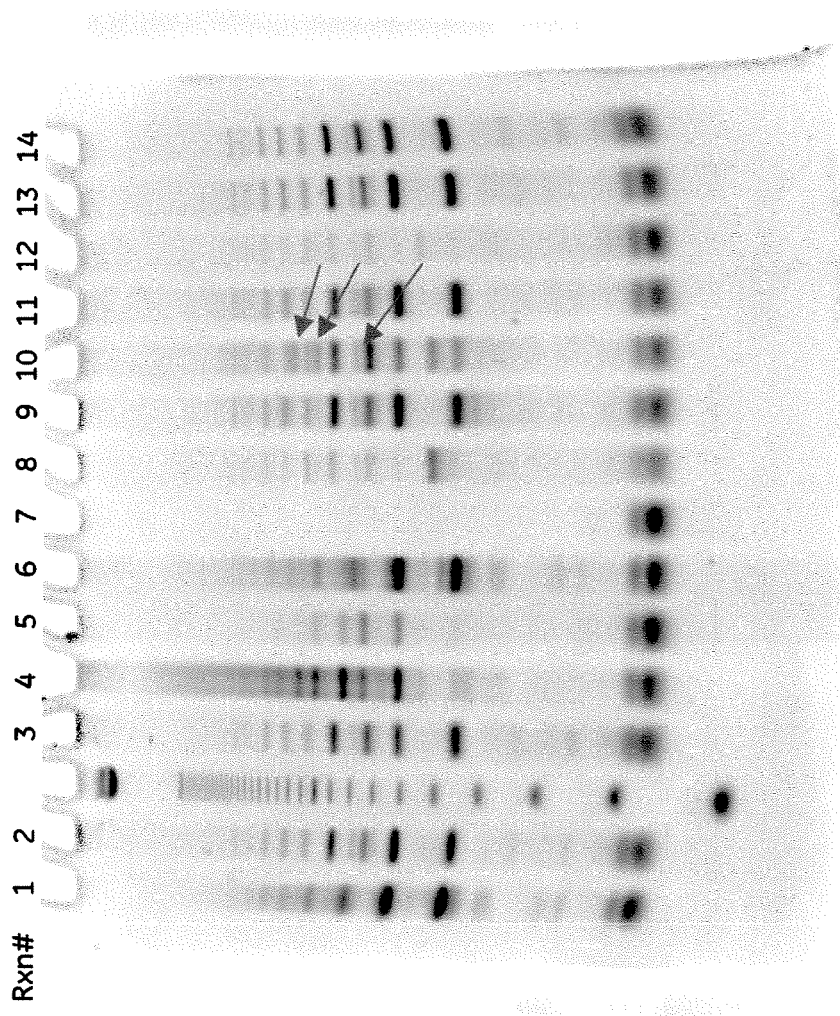
FIG. 8 depicts amplicon extension using an extension template as described in Example 7.

6 μl of "A" were added to reaction mixtures 1, 2, 4, 6, and 8-13; and 6 μl "B" were added to reaction mixtures 3, 5, 7, and 14. The resultant gel is depicted in FIG. 8.

Example 8

Genomic DNA

Reaction Scheme

TABLE 37

| Component | ID | | | | | | | | | | |
|---|---|---|---|---|---|---|---|---|---|---|---|
| | 1 | 2 | 3 | 4 | 5 | 6 | 7 | 8 | 9 | 10 | 11 |
| DNAG5 1:10 | − | + | + | + | + | + | − | − | − | − | − |
| B. cereus gDNA (100 ng/uL) | − | − | − | − | − | − | + | + | + | + | + |
| SYBR Green I (1:2000) | + | + | + | + | + | + | + | + | + | + | + |
| SSB (100 ng/uL) | − | − | + | − | − | − | − | + | − | − | − |
| SSB (10 ng/uL) | − | − | − | + | − | − | − | − | + | − | − |
| SSB (1 ng/uL) | − | − | − | − | + | − | − | − | − | + | − |
| SSB (0.1 ng/uL) | − | − | − | − | − | + | − | − | − | − | + |

Denaturations

TABLE 38

| Component | ID | | | | | | | | | | |
|---|---|---|---|---|---|---|---|---|---|---|---|
| | 1 | 2 | 3 | 4 | 5 | 6 | 7 | 8 | 9 | 10 | 11 |
| 10X HE Buffer | 3 | 3 | 3 | 3 | 3 | 3 | 3 | 3 | 3 | 3 | 3 |
| DNAG5 1:10 | — | 3 | 3 | 3 | 3 | 3 | — | — | — | — | — |
| B. cereus gDNA (100 ng/uL) | — | — | — | — | — | — | 3 | 3 | 3 | 3 | 3 |
| 4133-76OM | 1.5 | 1.5 | 1.5 | 1.5 | 1.5 | 1.5 | 1.5 | 1.5 | 1.5 | 1.5 | 1.5 |
| Water | 10.5 | 7.5 | 7.5 | 7.5 | 7.5 | 7.5 | 7.5 | 7.5 | 7.5 | 7.5 | 7.5 |
| Total Volume (μL) | 15 | 15 | 15 | 15 | 15 | 15 | 15 | 15 | 15 | 15 | 15 |

The reaction mixtures were heated 95° C. for 2 minutes and cooled to room temperature in the thermal cycler. And, 3 μL of the indicated SSB solution was added to the appropriate tubes.

Bulk Enzyme Mix

TABLE 39

| Component | 1X | 13X (X3) |
|---|---|---|
| 10X Rxn Buffer | 1 μL | 39 μL |
| 1:2000 SYBR Gold | 1 μL | 39 μL |
| 100% Ethylene Glycol | 1 μL | 39 μL |
| ΔTts | 1 μL | 39 μL |
| Endo V | 0.05 μL | 1.95 μL |
| Total Volume | 4.05 μL | 157.95 μL |

Figure 9:
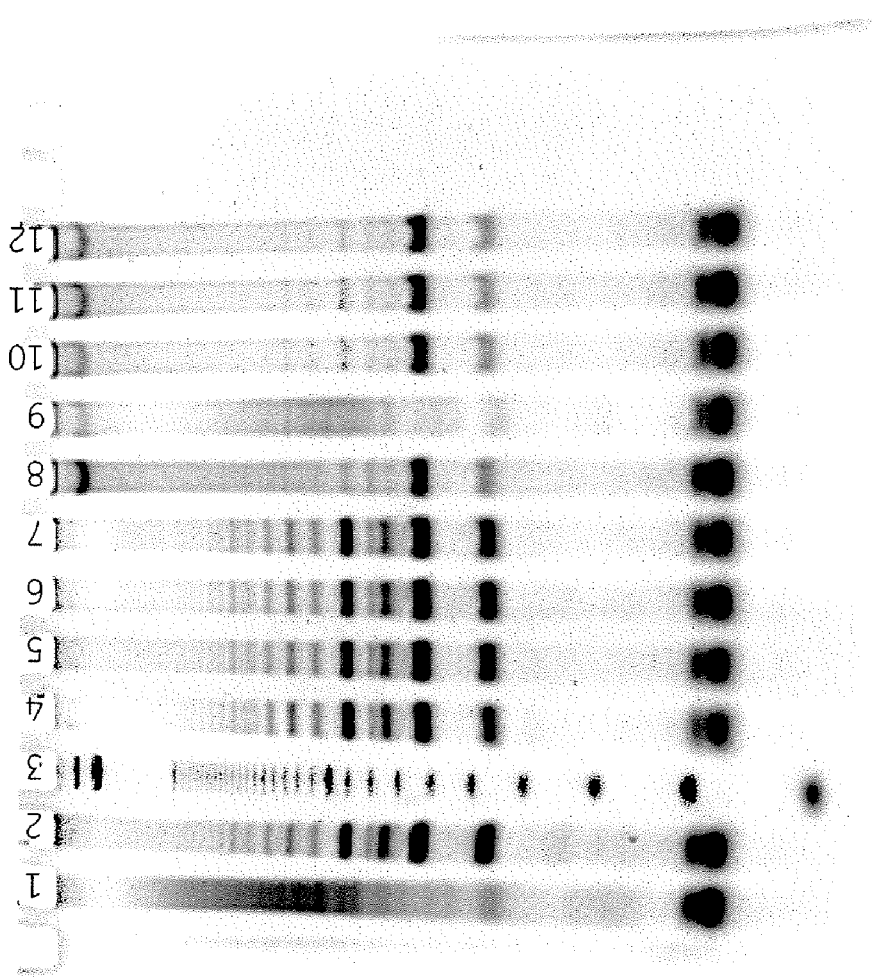
FIG. 9 depicts amplification using genomic DNA template as described in Example 8.

12 μL/reaction were cycled in an Applied Biosystems 7500 PCR System as follows: (1) Stage 1, 10 seconds at 44° C.; and (2) Stage 2, 50 seconds at 45° C. Stages 1 and 2 were repeated seventy five times and data was collected during stage 2. When completed, the reactions were stored at −20° C. overnight and then analyzed on a 10% TBE Urea gel, shown in FIG. 9.

Example 9

Effect of SSB on Amplification in the Presence of Contaminating DNA

The reaction mix contained 10 mM HEPES 7.9, 3 mM MgCl2, 0.25 mM dNTP, 1 mM DTT, 0.01% Tween, 10% ethylene glycol, 10% glycerol, 10 ng/μL E. coli SSB, 0.4 μM E. coli Endo V, with 19 U DTts. Reaction mixtures containing 0.5 ng of λ DNA, 5 ng λ DNA, 50 ng λ DNA, and the 6 primers shown in Table 40 (each primer at 1 μM concentration), were incubated with and without 100 ng of E. coli genomic DNA, and a titration of E. coli SSB was added as indicated in the chart at FIG. 10.

TABLE 40

| Oligo | 6 primers used in the reactions: | Length | SEQ ID NO: |
|---|---|---|---|
| 7290R | AGTTCTTCTTTCGTCCCCIT | 20 | 32 |
| 7270R | CAGGCTGACATCACIIT | 17 | 33 |
| 7253R | TCAGTTGTTCACCCAGCIA | 19 | 34 |

TABLE 40-continued

| Oligo | 6 primers used in the reactions: | Length | SEQ ID NO: |
|---|---|---|---|
| 7062F | ACCACCGGCGATCCIIC | 17 | 38 |
| 7079F | GCGTGAGTTCACCATIA | 17 | 39 |
| 7114F | TGCTGCTGGCTGACCCTIA | 19 | 53 |

Figure 10:
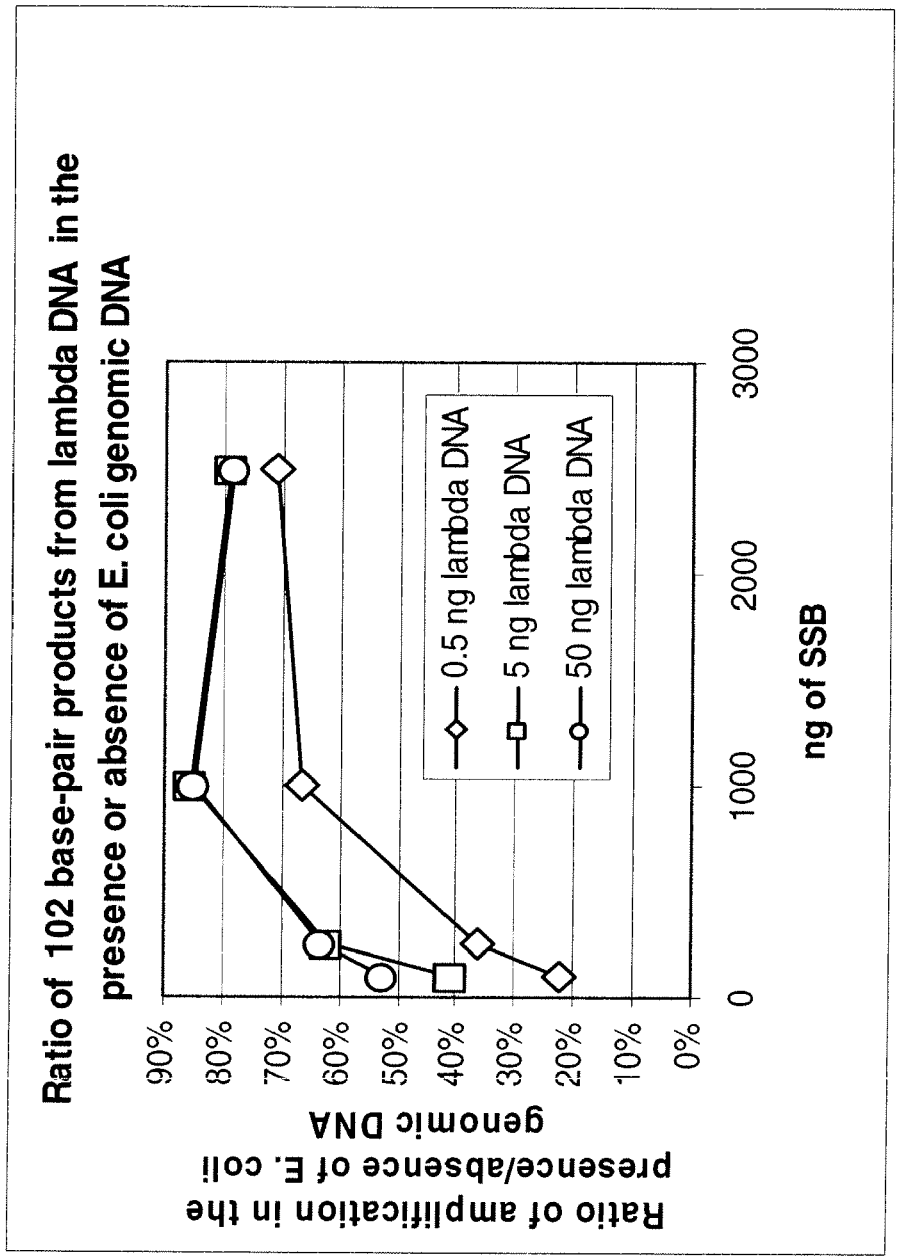
FIG. 10 shows amplicon generation from lambda DNA and the effects of contaminating DNA as described in Example 9.

Template and primers were pre-annealed by denaturation at 95° C. for 2 min then placed at room temperature, and then mixed with the rest of reaction components. Reactions were incubated for 80 min at 45° C. and products were separated on TBE-Urea gel. Gels were stained using SYBR gold and scanned on Typhoon scanner. As shown in FIG. 10, the SSB enhanced amplification of product in the presence of contaminating genomic DNA.

Example 10

Generation and Expression of Y73A endo V

The original plasmid encodes wild type E. coli endo V in pET22b+ as a terminal HIS tagged fusion construct, flanked by an NdeI site at the initiation and a XhoI site at the termination sequence. PCR was performed using primer "endo V us" with "endo V int ds" to make a 215 base pair gene fragment. This fragment was restricted using NdeI and NgoI to generate cohesive ends. PCR was performed using primer "endo V ds" with "endo V int us" to make a 457 base pair gene fragment. This fragment was restricted using NgoI and XhoI to generate cohesive ends. The fragments were ligated in a "3-way" reaction containing pET22b+ that had been linearized with NdeI and XhoI. After transformation into host *E. coli* strain JM109 (DE3), a clone was sequenced to confirm mutagenesis.

Protein was expressed and purified by standard techniques: Transformed *E. coli* JM109 (DE3) was grown in 2×YT medium and protein expression induced with IPTG. Protein was extracted into lysis buffer consisting of 10 mM HEPES buffer (pH 8), 1 M NaCl, 0.1% TritonX-100, 0.1% Tween-20, 10 mM β-ME, 5% glycerol, 10 mM Imidazole, with Roche "Complete" protease inhibitors. Sonication was used to disrupt the cells, and the extract clarified by centrifugation before application of the Ni-NTA resin. Captured protein was eluted into lysis buffer with 200 mM Imidazole. Batch mode capture, wash, and elution on Ni-NTA resin were preformed according to manufacturer recommendations (Qiagen Corp.). The eluate was dialyzed and stored in a buffer consisting of 10 mM HEPES buffer (pH 8), 150 mM NaCl, 0.1 mM EDTA, 0.01% TritonX-100, and 50% glycerol.

Example 12

Mutant Endo V Performance Characteristics

Figure 11:
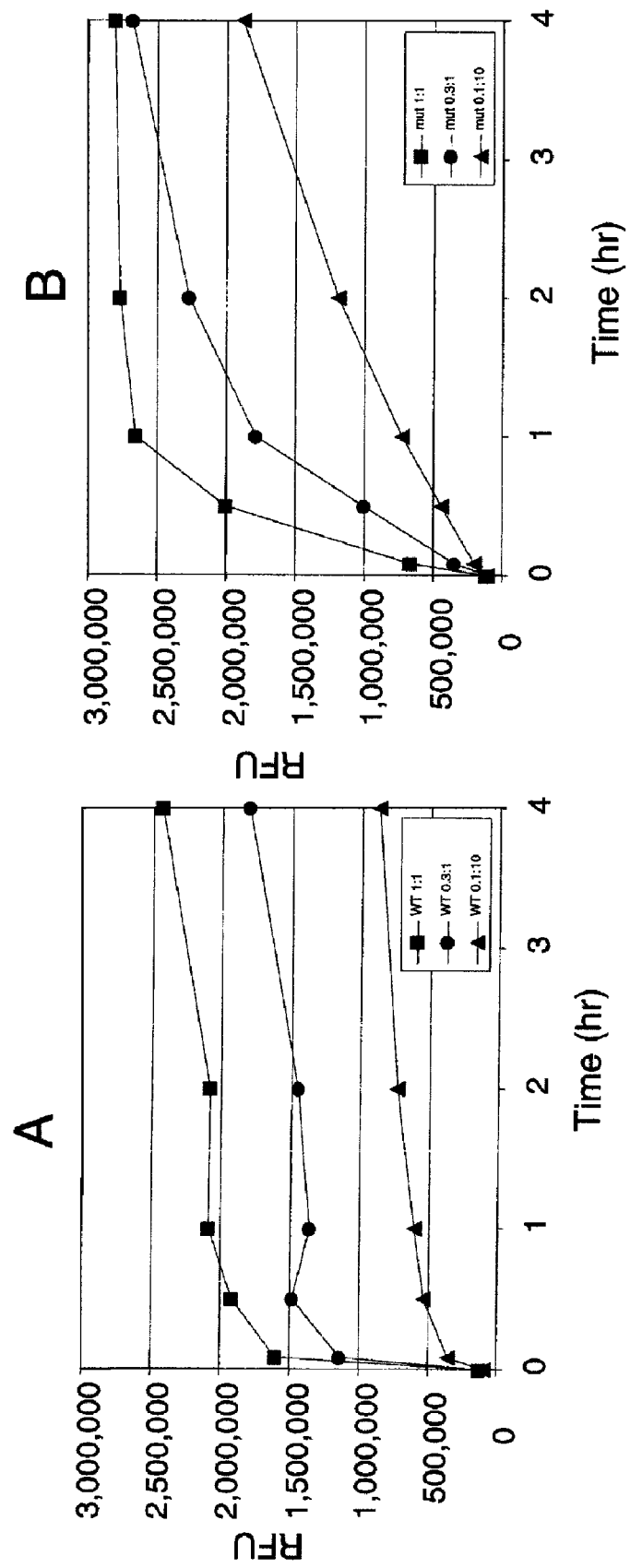
FIG. 11 depicts the relative activities of the WT endonuclease V to the activity of the mutant endonuclease V as described in Example 12.

Reactions containing (25 mM Tris:borate 8.1, 5 mM MgCl, 1 mM DTT, 0.01% tween-20) and 1 pmole of FAM-I primer (SEQ ID NO.: 24) and 1 pmole HEX-C oligo (SEQ ID NO.: 25), pre-annealed, were incubated at 37° C. for (0, 5, 30, 60, 120, and 480 minutes) with either (1, 0.3, or 0.1 pmoles of) wild type or Y75A mutant *E. coli* endo V as indicated. Reactions were resolved by denaturing acrylamide gel electrophoresis and gels visualized by scanning on a Typhoon 9410. The small molecular weight nicked product was quantified and the relative fluorescence was compared and depicted in FIG. 11. Results indicate that the mutant enzyme supports repeated nicking by each enzyme, while the wild type enzyme seems capable of only a single round of nicking.

Example 13

Mutant Endo V Inosine Specificity

Reaction mixtures containing (25 mM Tris HCl 8.5, 5 mM MgCl, 1 mM DTT, 0.01% tween20, 10% glycerol) were prepared with 200 ng of either HindIII linearized pUC18 DNA or 200 ng of HindIII restricted pUC18 DNA that had been amplified using a modified rolling circle amplification reaction in which the dGTP has been substantially replaced with dITP to generate amplified material containing dIMP in place of dGMP, as indicated.

To the reaction was added either wild type or mutant *E. coli* endo V as indicated (0, 0.01, 0.1, or 1 microgram of protein), and incubated at 37° C. for 90 minutes. Reactions were then visualized by denaturing agarose gel electrophoresis, staining with SYBR gold and scanning on the Typhoon 9410. Results shown in FIG. 12 indicate that both wild type and mutant enzyme have at least 100× increased nicking activity toward inosine-containing DNA.

Example 14

Mutant Versus Wild Type Endonuclease

Time course of amplification was studied in reaction mix containing 10 mM Tris, pH 8.3, 2 mM MgCl$_2$, 0.01% Tween-20, 200 μM dNTP's, 10% Ethylene Glycol, 2 mM DTT, 25 ng/μL SSB, 10 nM Bst polymerase, Large Fragment, and 10 nM *E. coli* Endo V Y75A mutant. DNA substrate was 10 ng or 15 fmol of approximately 1 kb size PCR products made with I or G (penultimate base to 3' end) containing PCR primers. Reactions were stopped at 15, 30, 60, 120, 240, 480, and 1260 min., by adding EDTA to 10 mM and samples were run on a 1% alkaline agarose gel to separate amplification products. Gels were then neutralized and stained with SYBR gold and scanned and quantified on Typhoon 9410 and ImageQuant image analysis software, as shown in FIG. 13.

TABLE 41

| Name | Sequence | Length | SEQ ID NO: |
|---|---|---|---|
| Forward primer 40FGI | GTTTTCCCAGTCACGACGTT GTAAAACGACGICC | 34 | 47 |
| Reverse primer: | TCAAAGAAGTATTGCTACAAC GG | 23 | 48 |
| Forward primer: 40FGG | GTTTTCCCAGTCACGACGTTG TAAAACGACGGCC | 34 | 49 |
| Reverse primer: | TCAAAGAAGTATTGCTACAAC GG | 23 | 50 |

Example 15

Kinetics of Amplification: Comparison of *E. coli* Y75A Mutant Endo V versus Afu. Y74A Mutant Endo V

TABLE 42

| Name | Sequence | Length | SEQ ID NO: |
|---|---|---|---|
| Tban-1 DNA Template | CAATAGACTCCATACCACCA ATTGTAATTTCTGTACGTCT CTTATCATTGAAGCGCTCTT TTACTTCTGTTAATTCTTCA CGAATAATCTCAAGAACCTT TTCTTCATCTGC | 112 | 54 |
| Tban-1 forward primer: | GCAGATGAAGAAAAGGTTCT TGAGATTATTCIT | 33 | 51 |
| Tban-1 reverse primer | CAATAGACTCCATACCACCA ATTGTAATTTCTIT | 34 | 55 |

Amplification reactions were carried out in reaction mix containing 10 mM Tris, pH 8.3, 3 mM MgCl$_2$, 0.01% Tween-20, 250 μM dNTP's, 10% Ethylene Glycol, 1 mM DTT, 50 nM Bst polymerase, Large Fragment, or T. ma polymerase (100 ng), and 0.8 μM *E. coli* Endo V, Y75A mutant or 0.4 μM A. fu, Endo V, Y75A mutant. Both forward and reverse primers were maintained at 0.25 μM and template at 0.1 μM.

Reactions were incubated for 80 min at 45° C. and products were separated on TBE-Urea gel. Gels were stained using SYBR gold and scanned on Typhoon scanner as shown on FIG. 14.

Example 16

Thermal Stability of Mutant endo V

*E. coli* Mut Endo V at a concentration of 1.6 μM was incubated at following temperatures: on ice, 37° C., 40° C., 43° C., 46° C., 49° C., 52° C., 55° C., and 58° C. for different amount of times such as 15, 30, 45, 60, and 75 min., in buffer containing 10 mM HEPES 7.9, 3 mM $MgCl_2$, 0.25 mM dNTP, 1 mM DTT, 0.01% Tween, 10% ethylene glycol, and 0.5 µL ThermoFidelase (Fidelity Systems).

At time points indicated above samples were removed from the incubator and put on ice until all incubations were completed. To these pre-incubated samples following reaction components were added (10 mM HEPES 7.9, 0.25 mM dNTP, 1 mM DTT, 0.01% Tween, 10% ethylene glycol) and P1/P2-1/P3 primer mix (to 0.2/1/1.8 µM each), 0.5 nM template, 10 ng/µL of T4 g32 protein, 5U Klenow exo-polymerase.

All reactions were then incubated at 45° C. for 80 min. Products were separated on TBE-Urea gel, that were stained using SYBR gold and scanned on Typhoon scanner (shown as FIG. 15).

Example 17

Real Time Analysis of Amplicon Generation

A dilution series of lambda DNA was prepared in HETB buffer (10 mM HEPES 7.9, 0.1 mM EDTA, 0.01% tween-20, 0.5 mg/ml BSA) and 10 pmoles each of the following primers: (7062F, 7079F, 7096F, 7111F, 7127F, 7144F, 7290R, 7270R, 7253R, 7234R, 7215R, 7194R, shown below in Table 43) and heat denatured for 2 minutes at 95° C. and then chilled on ice.

TABLE 43

| Oligo | Length |
|---|---|
| 7290R | 20 |
| 7270R | 17 |
| 7253R | 19 |
| 7234R | 19 |
| 7215R | 17 |
| 7194R | 19 |
| 7062F | 17 |
| 7079F | 17 |

TABLE 43-continued

| Oligo | Length |
|---|---|
| 7096F | 18 |
| 7111F | 16 |
| 7127F | 17 |
| 7144F | 15 |
| T7-7158F-misA: | 50 |
| Quencher-oligo | 24 |
| Dye-oligo | |

A mix containing components was then added to a final concentration of: 35 units delta Tts, 8 pmoles *E. coli* endo V Y75A, 0.002 mg SSB, 3 mM MgCl, 0.1 mM MnSO4, 3 pmole ROX std dye, 1× buffer (20 mM HEPES 7.9, 0.25 mM dNTP, 1 mM DTT, 0.01% Tween, 10% glycerol, and 10% ethylene glycol. Then 3 pmoles T7-7158F-misA, 4 pmoles quencher-oligo, 2.5 pmoles dye-oligo were mixed in HET buffer, heated to 95 degrees for 45 seconds and slow cooled to ice over 5 minutes and added to the amplification reaction.

The reactions were cycled an ABI 7500 75 times (46° C., 50 seconds; 45° C., 10 second), taking readings during the 46° C. step. This 1° C. cycle was employed because the ABI machine does not hold reactions at a single temperature. A 75-minute incubation was performed and data was exported to excel. The time at which each reaction produced a signal above a threshold level was plotted on a semi log scale. A linear curve was generated (shown in FIG. 16), indicating that the reaction gave reliable quantification over at least 5 orders of magnitude.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:
1. An amplicon production kit comprising:
   at least one inosine-containing primer;
   at least one exonuclease-deficient DNA polymerase with strand displacement activity; and
   at least one nuclease, which is capable of nicking DNA at a residue 3' to an inosine residue.
2. The amplicon production kit of claim 1, wherein the at least one inosine-containing primer comprises multiple forward and reverse primers.
3. The amplicon production kit of claim 2, further comprising at least one extender template.
4. The amplicon production kit of claim 1, wherein the inosine is positioned at least 4 nucleotides from the 5' end of the at least one inosine-containing primer.
5. The amplicon production kit of claim 1, wherein the at least one nuclease comprises an endonuclease V.
6. The amplicon production kit of claim 1, wherein the at least one exonuclease-deficient DNA polymerase is selected from exonuclease deficient T7 DNA polymerase, exo(−) Klenow, or combinations thereof.
7. The amplicon production kit of claim 5, wherein the endonuclease V is selected from a protein, the sequence of which consists of SEQ ID NO.: 1, SEQ ID NO.: 2, SEQ ID NO.: 3, or conservative variants thereof.
8. The amplicon production kit of claim 1, further comprising a dNTP mixture consisting of dTTP, dGTP, dATP, and dCTP, or analogs thereof.
9. The amplicon production kit of claim 1, further comprising a chemical denaturant selected from glycerol, ethylene glycol, or formamide.
10. The amplicon production kit of claim 1, further comprising a buffer is selected from Tis, HEPES, or MOPS.
11. The amplicon production kit of claim 10, wherein the buffer includes a surfactant selected from Tween-20, NP-40, Triton-X-100, or a combination thereof.
12. The amplicon production kit of claim 1, further comprising a divalent cation selected from $Mn^{+2}$, $Mg^{+2}$, or a combination thereof.
13. The amplicon production kit of claim 12, wherein the divalent cation comprised $MgCl_2$ present in the reaction mixture at a final concentration of 2 mM to 6 mM.
14. The amplicon production kit of claim 1, further comprising a reducing agent.
15. The amplicon production kit of claim 14, wherein the reducing agent is selected from dithiothreitol (DTT), 2-mercaptoethanol (βME), 2-mercaptoethylamine (MEA), or Tris (carboxyethyl) phosphine (TCEP).
16. The amplicon production kit of claim 1, further comprising at least one single stranded DNA binding protein.
17. The amplicon production kit of claim 16, wherein the at least one single stranded DNA binding protein is selected from *E. coli* SSB, T4 gene 32 protein, T7 gene 2.5 protein, Ncp7, recA, or combinations thereof.
18. The amplicon production kit of claim 1, further comprising at least one blocking agent including albumin.
19. The amplicon production kit of claim 1, further comprising at least one topoisomerase.
20. The amplicon production kit of claim 1, wherein the at least one inosine-containing primer is 5 to 100 nucleotides in length, 5 to 30 nucleotides in length, or 5 to 20 nucleotides in length.
21. The amplicon production kit of claim 1, wherein the at least one inosine-containing primer demonstrates a melting temperature of 25° C. to 70° C., 30° C. to 65° C., or 40° C. to 55° C.
22. The kit of claim 1, wherein the at least one nuclease is incapable of degrading the at least one inosine-containing primer.

* * * * *